United States Patent
Gueller et al.

(10) Patent No.: US 7,996,107 B2
(45) Date of Patent: *Aug. 9, 2011

(54) DEVICE HAVING A TOOL HOLDER, A TOOL AND A BALANCE

(75) Inventors: Rolf Gueller, Herznach (CH); Josef Schröer, Muttenz (DE); Paul Frank, Ennetbürgen (CH); Franz Metzger, Basel (CH); Christoph Bachmann, Lausen (CH); Gerhard Klokow, Rheinfelden (DE); Benard Zahnd, Riehen (CH)

(73) Assignee: Chemspeed Technologies AG, Augst (CH)

(*) Notice: Subject to any disclaimer, the term of this patent is extended or adjusted under 35 U.S.C. 154(b) by 0 days.

This patent is subject to a terminal disclaimer.

(21) Appl. No.: 10/381,555

(22) PCT Filed: Oct. 4, 2001

(86) PCT No.: PCT/CH01/00600
§ 371 (c)(1),
(2), (4) Date: Jul. 14, 2003

(87) PCT Pub. No.: WO02/29369
PCT Pub. Date: Apr. 11, 2002

(65) Prior Publication Data
US 2004/0044439 A1   Mar. 4, 2004

(30) Foreign Application Priority Data
Oct. 6, 2000  (CH) .................................. 1980/00

(51) Int. Cl.
G06F 17/00  (2006.01)
(52) U.S. Cl. ........... 700/240; 414/21; 422/63; 422/931; 422/62; 422/67; 422/68.1; 222/77; 436/43; 483/902; 702/129; 702/173; 702/174; 702/175

(58) Field of Classification Search .................... 414/21; 294/16; 483/902; 700/240; 422/63, 931, 422/22, 62, 67, 68.1, 43, 48; 222/77; 453/43–54; 436/43, 46–54; 435/43–54; 702/33, 113–115, 702/94, 95, 127, 129, 150, 152, 173–175
See application file for complete search history.

(56) References Cited

U.S. PATENT DOCUMENTS
3,321,116 A * 5/1967 Loftin ........................... 222/595
(Continued)

FOREIGN PATENT DOCUMENTS
DE         3617595 A1   11/1987
(Continued)

OTHER PUBLICATIONS
NPL abstract translation of JP11-014630a.*
(Continued)

Primary Examiner — Jeffrey A Shapiro
(74) Attorney, Agent, or Firm — Husch Blackwell LLP

(57) ABSTRACT

The invention relates to a device that comprises a tool holder that can be adjusted in an x-axis, a y-axis which is perpendicular thereto, and a z-axis that is perpendicular both to the x-axis and the y-axis and that can be pivoted about the z-axis. A dispense head for solid material is mounted on the tool holder as the tool. Two scales are disposed on the dispense head for solid material, said scales weighing the material which is or is to be delivered by the dispense head for solid material. The inventive design with two scales directly mounted on the dispense head for solid material allows for weighing of the material without the dispense head for solid material or the material having to be placed on separate scales.

28 Claims, 14 Drawing Sheets

U.S. PATENT DOCUMENTS

| | | | |
|---|---|---|---|
| 4,171,067 A | | 10/1979 | Faulkner et al. |
| 4,337,878 A | | 7/1982 | Brock |
| 4,413,691 A | | 11/1983 | Wetzel |
| 4,451,433 A | * | 5/1984 | Yamashita et al. .............. 422/63 |
| 4,804,111 A | | 2/1989 | Ricciardi et al. |
| 4,805,673 A | | 2/1989 | Wöhrle et al. |
| RE32,920 E | * | 5/1989 | Matson et al. ............. 205/789.5 |
| 4,880,142 A | | 11/1989 | Higuchi et al. |
| 4,913,198 A | * | 4/1990 | Hayahara et al. ............... 141/83 |
| 4,959,947 A | | 10/1990 | Reif |
| 4,976,377 A | | 12/1990 | Higuchi et al. |
| 5,038,839 A | | 8/1991 | Morimoto et al. |
| 5,067,553 A | | 11/1991 | Nakajima |
| 5,150,530 A | * | 9/1992 | Schweitzer et al. ............ 33/626 |
| 5,209,361 A | * | 5/1993 | Grubb, Jr. ...................... 212/283 |
| 5,287,896 A | | 2/1994 | Graffin |
| 5,363,885 A | | 11/1994 | McConnell et al. |
| 5,428,993 A | * | 7/1995 | Kobashi ........................... 73/149 |
| 5,431,201 A | * | 7/1995 | Torchia et al. ................... 141/98 |
| 5,476,638 A | * | 12/1995 | Sulzbach ...................... 422/133 |
| 5,532,942 A | | 7/1996 | Kitamura et al. |
| 5,599,500 A | | 2/1997 | Jones |
| 5,660,792 A | * | 8/1997 | Koike .............................. 422/63 |
| 5,738,153 A | * | 4/1998 | Gerling et al. ................... 141/83 |
| 5,756,304 A | | 5/1998 | Jovanovich |
| 5,835,982 A | * | 11/1998 | Lanaro et al. .................. 177/145 |
| 5,873,394 A | * | 2/1999 | Meltzer ......................... 141/130 |
| 6,033,911 A | * | 3/2000 | Schultz et al. ................... 436/49 |
| 6,043,097 A | * | 3/2000 | Dumitrescu et al. ............ 436/48 |
| 6,121,049 A | * | 9/2000 | Dorenkott et al. .............. 436/50 |
| 6,132,582 A | * | 10/2000 | King et al. ..................... 204/604 |
| 6,358,749 B1 | * | 3/2002 | Orthman ........................ 436/177 |
| 6,374,982 B1 | * | 4/2002 | Cohen et al. ............... 198/346.2 |
| 6,539,334 B1 | * | 3/2003 | Sawafta ......................... 702/175 |
| 6,674,022 B2 | * | 1/2004 | Fermier et al. ................... 177/60 |
| 6,898,549 B1 | * | 5/2005 | Sawafta ......................... 702/175 |
| 2003/0077387 A1 | * | 4/2003 | Brynolf et al. ................. 427/223 |
| 2004/0022680 A1 | * | 2/2004 | Gueller et al. ................... 422/62 |

FOREIGN PATENT DOCUMENTS

| | | | |
|---|---|---|---|
| DE | 3801218 A1 | | 8/1988 |
| DE | 3801218 A1 | | 8/1988 |
| DE | 4002255 A1 | | 8/1991 |
| DE | 199 07 619 A1 | | 2/2000 |
| DE | 1985150 C1 | | 9/2000 |
| EP | 0 353 197 A1 | | 1/1990 |
| FR | 2 310 710 | | 12/1976 |
| FR | 2 749 662 | | 12/1997 |
| GB | 2 151 800 A | | 7/1985 |
| GB | 2 284 901 A | | 6/1995 |
| JP | 03202720 A | | 9/1991 |
| JP | 405-220691 A | * | 8/1993 |
| JP | 411014630 | * | 1/1999 |
| WO | WO 98/25695 | | 6/1998 |
| WO | WO 00/08472 | | 2/2000 |
| WO | WO 02/29419 A2 | | 4/2002 |

OTHER PUBLICATIONS

NPL translation of JP11-014630.*
NPL translation of JP405220691.*
NPL abstract translation of JP405220691.*
Notice of Opposition to a European Patent (EP 1 322 923) May 30, 2007, 51 pages.
EPA United States Environmental Protection Agency Quality Systems and Implementation Plan for Human Exposure Assessment.
EPA United States Environmental Protection Agency, Field Operations Protocol.
RTI/ACS-209-010.
EPA Innovative Technology Verification Report.
The Milestone DMA-80.
EPA Method Analytical BalanceTable.
EPA Traceability Protocol for Assay and Certification of Permeation Device Calibration Standards.
Mettler Brochure 2005.
Mettler Brochure 2007.
Mettler Toledo, Weighing Tables.
Weighing Table MCP2.
Weighing Table XP26PC.
Steiner Environmental, Inc. AP-42 Section Number Emission Testing on Two Baghouses at Harris Woolf California Almonds.
Sartorius Correct Use and Handling of Analytical and Microbalances.
Sartorius Basic—Electronic Semi-micro, Analytical and Precision Balances, Installation and Operating Instructions.
Sartorius Balances Tables and Wall Consoles.
Brief in response to the submission of the patent proprietor dated Jul. 15, 2008, European opposition proceedings and documents filed therewith.
Powdernium AD: Operating and Maintenance Instruction (2000) 12 pages.
Bohdan: Caco-2 Assay Workstation (www.bohdan.com/caco2.htm) Product Highlights and Capabilities (Sep. 19, 2000) 3 pages.
The AutoDose L1000 Powder Dispenser (www.scitec-automation.ch)/autodose.htm) (May 12, 2000) 1 page.
Quad-Z215: High throughput Liquid Handler and Injector with four independent probes (www.gilson.com/c250spec.htm) (Aug. 8, 2000) 7 pages.
Genesis—Robotic Sample Processor (www.tecan.com/tec_rsp.htm) (Sep. 19, 2000) 4 pages.
Tecan MiniPrep Series Robotic Sample Processors 2 pages.
Powdernium 1.3x User Manual (2000) 18 pages.

* cited by examiner

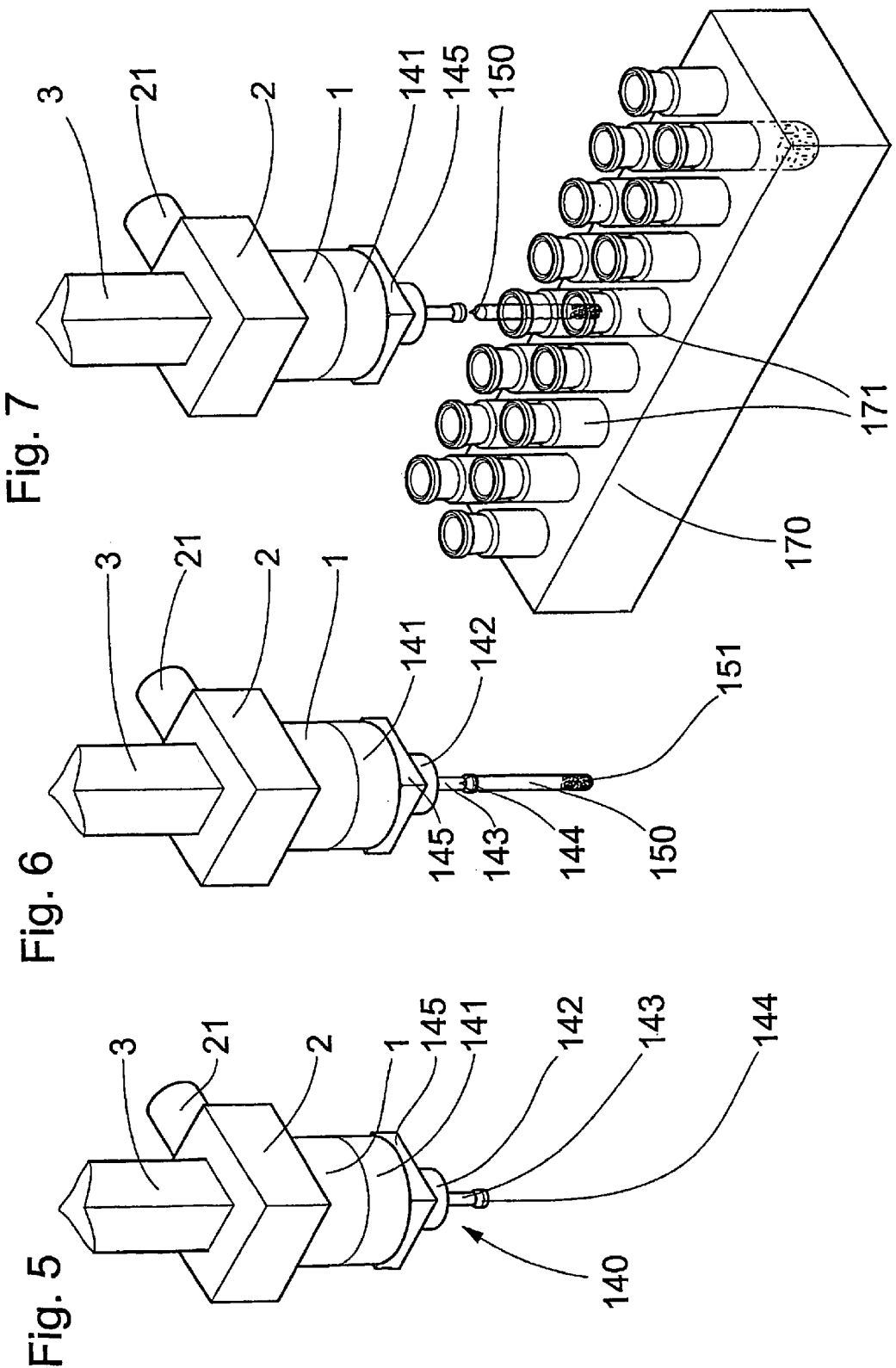

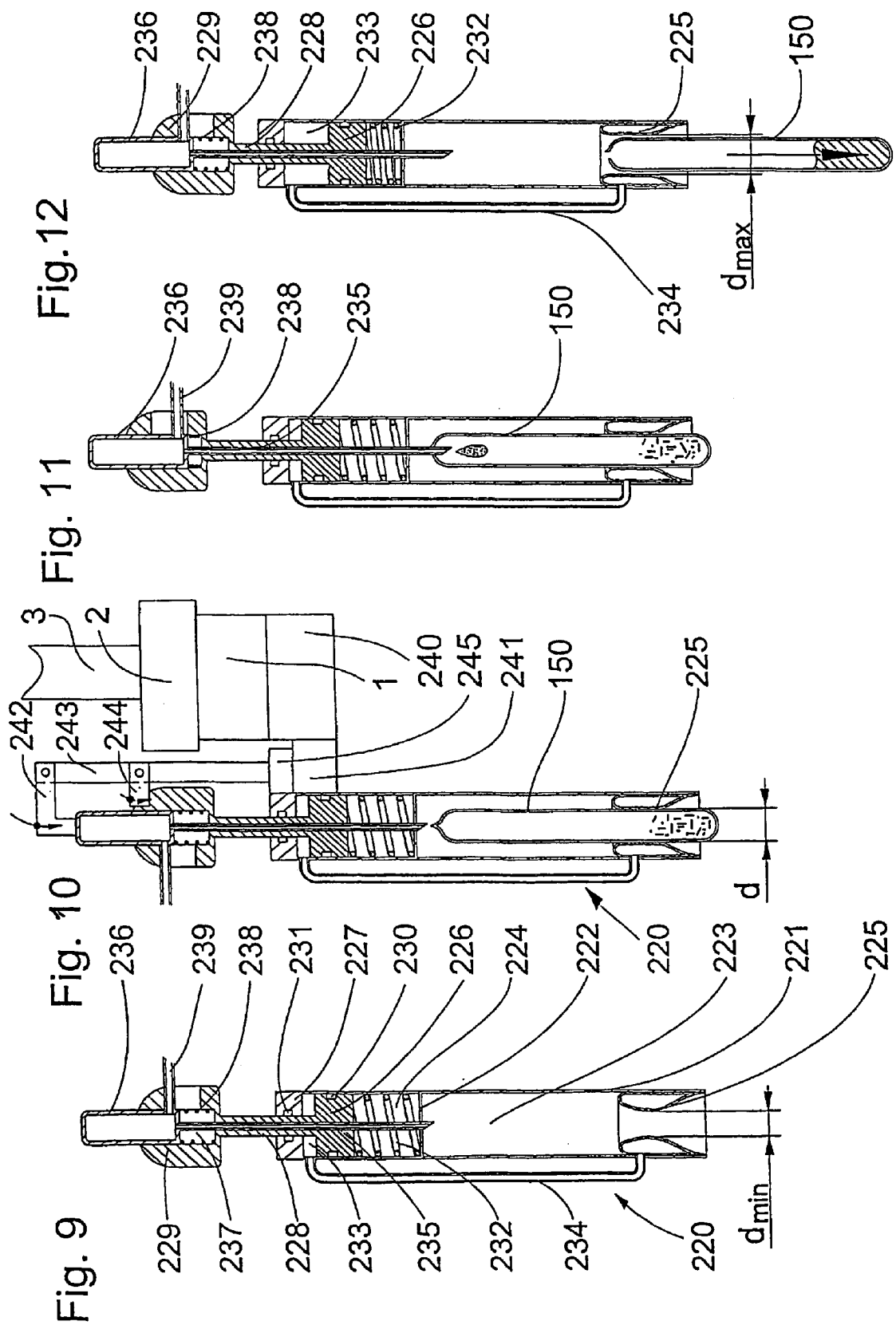

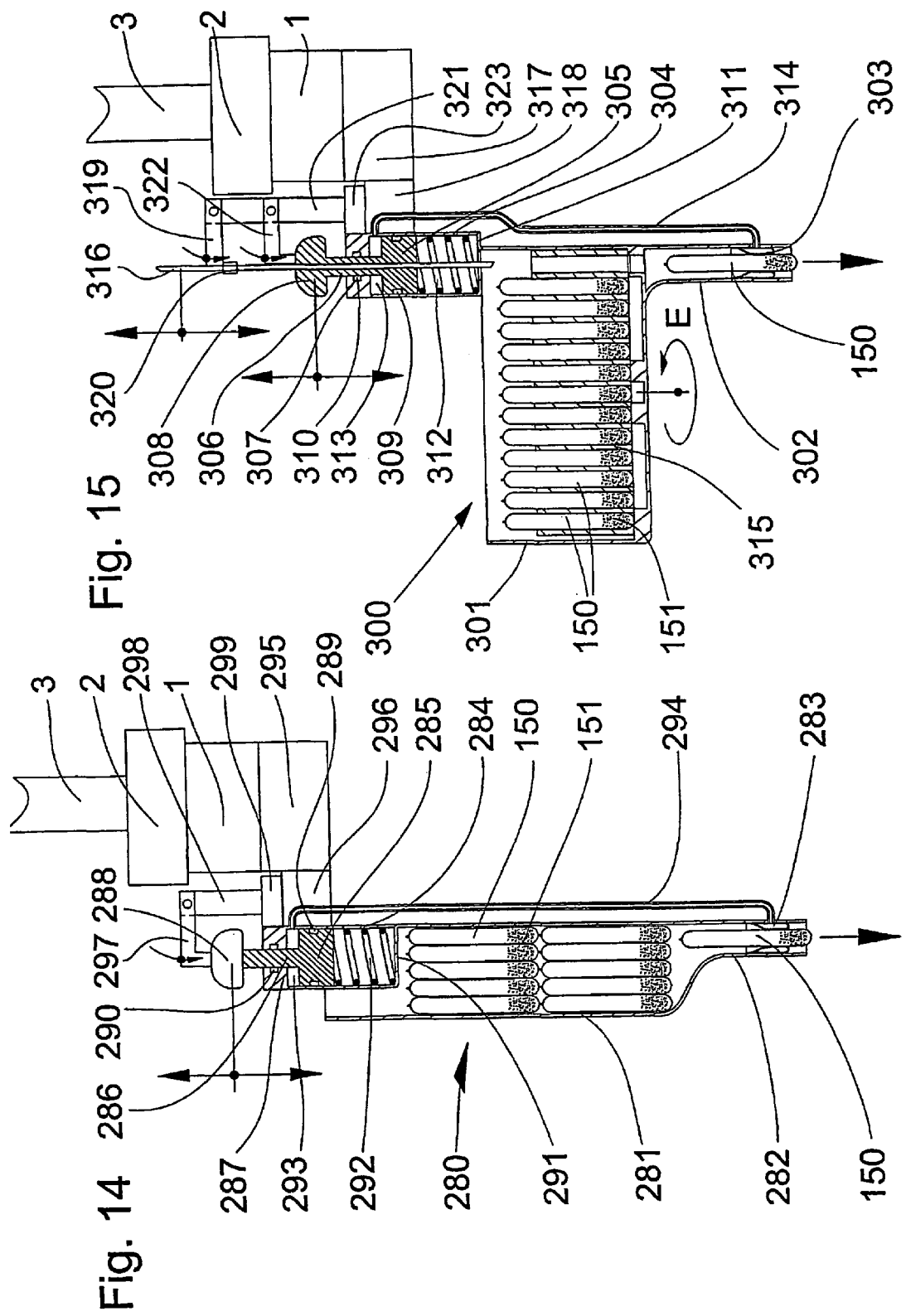

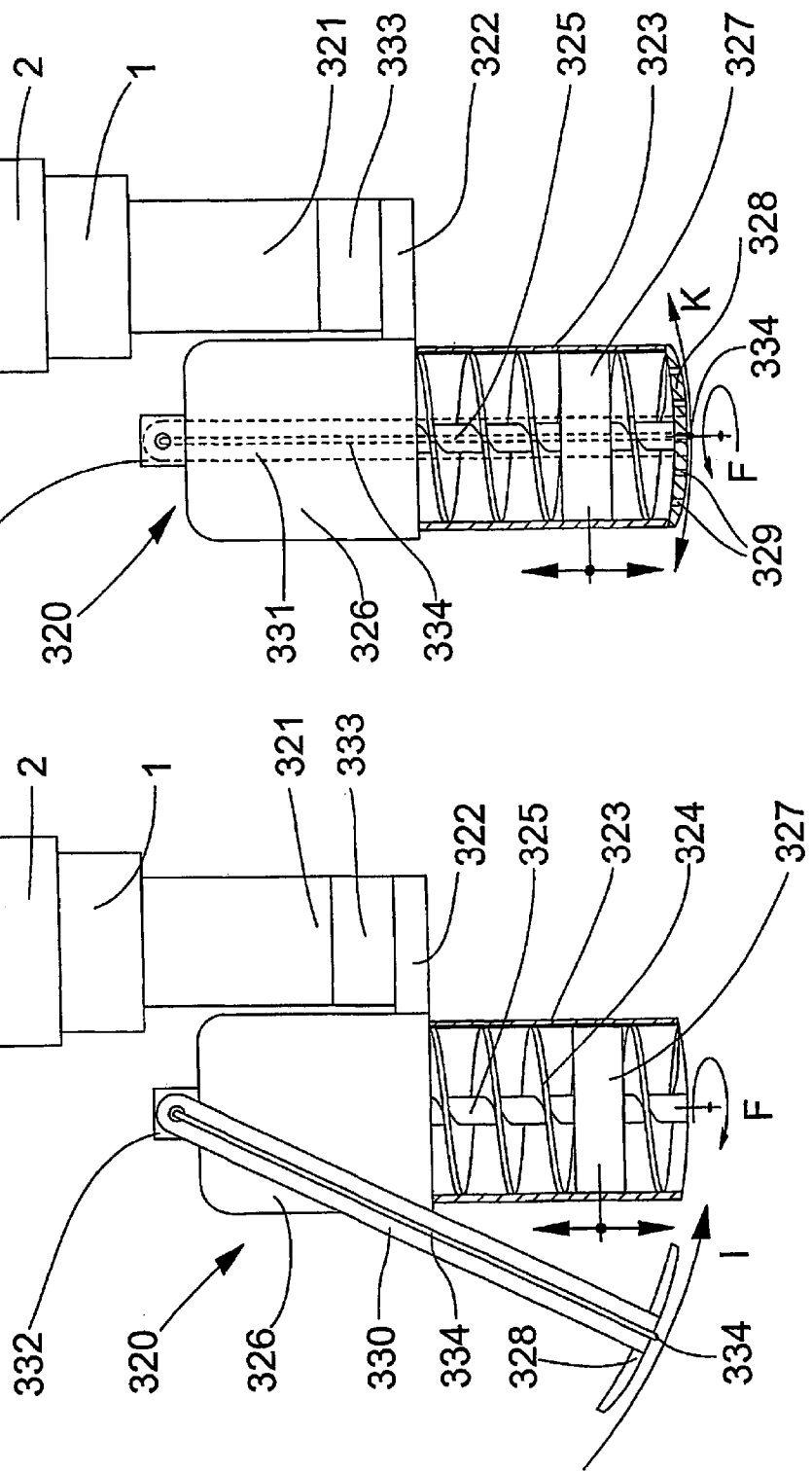

DEVICE HAVING A TOOL HOLDER, A TOOL AND A BALANCE

BACKGROUND OF THE INVENTION

The invention relates to a device having a tool holder, which can be displaced in an x direction and a z direction which is perpendicular to the x direction, and a tool in the form of a metering head, which is secured to the tool holder. A further aspect of the invention relates to weighing out a desired quantity of substance using a device of this type.

Devices of this type are used, inter alia, for automatically metering substances into a plurality of reaction vessels or test tubes which are arranged, for example, next to one another.

In a device which is known as Caco-2 Assay produced by Mettler Toledo Bohdan, Greifensee, Switzerland, there are two tool holders with different tools. The tool holders can be displaced in a horizontal x direction, a horizontal y direction which is perpendicular to the x direction, and a vertical z direction which is perpendicular to the x and y directions, and in this way can serve reaction vessels arranged next to one another under the control of software. One of the tools is designed for metering liquid as a metering head in the form of a four-needle head with four parallel hollow needles which can be spread apart. The other tool is a gripper for handling substance plates which have a multiplicity of recesses for holding substance. To weigh matter which can be handled by the device, there is a balance, on which, by way of example, a corresponding substance plate or a test tube is placed.

Although the two fixedly installed tools do make it possible to handle liquids and solids, they do not, for example, allow a solid to be metered directly into a reaction vessel. Moreover, there are two tool holders which have to be able to move independently of one another, in which context it must be ensured that they do not collide with one another. Finally, accurate weighing out of a defined quantity of substance is relatively complex.

DE 40 02 255 A1 has disclosed a fixedly mounted device for metering liquids by dispensing them from at least one metering valve connected to a liquid reservoir, which device has a main balance on which a vessel for holding liquid can be positioned. This main balance has a wide weighing range of, for example, several tons and therefore a relatively low accuracy of, for example, ±100 g. Between the metering valve and the liquid reservoir there is a buffer vessel, the weight of which can be determined by means of a precision balance and which can be sealed off with respect to the liquid reservoir in order to dispense small quantities of liquid from the metering valve. The precision balance can be used to determine the weight of the buffer vessel and the liquid which is present therein, according to the disclosure with an accuracy of, for example, ±0.1 g, and from this determination to determine the quantity of liquid which has been dispensed. The accuracy of the weight of the quantity of liquid dispensed is limited firstly by the fact that the buffer vessel is connected to the storage reservoir and the metering valve via flexible lines, which has an adverse effect on the measurement, and secondly by the fact that the liquid is not dispensed directly from the buffer vessel, but rather firstly passes via a line to the metering valve and is only dispensed by the latter. Moreover, the complex structure with storage vessel, buffer vessel and metering valve, which are connected via lines, in practice prevents the metering device from being of mobile design or being fitted to a robot arm or a linear axis system.

In view of the drawbacks of the devices of the prior art which have been described above, the invention is based on the object of providing a device which is intended to allow simplified weighing out of a desired quantity of substance.

SUMMARY OF THE INVENTION

The essence of the invention consists in the fact that, in a device having a tool holder, which can be displaced in an x direction and a z direction which is perpendicular to the x direction, and a tool in the form of a metering head, which is secured to the tool holder, a balance, by means of which substance or capsules which has/have been taken up or dispensed or is/are to be dispensed by the tool can be weighed, is arranged on the tool or on the tool holder.

The fact that a balance is arranged directly on the tool or on the tool holder allows a substance which has been taken up or dispensed or is to be dispensed, a substance capsule or another object to be weighed without the substance, the substance capsule or the other object or the tool for this purpose having to be placed onto a separate balance. This significantly simplifies the weighing operation and also means that the weighing is virtually location-independent within the range of action of the device and can even take place where, for technical reasons, it is difficult or impossible to position a balance, for example beneath a shaken reaction vessel.

The balance used may, for example, be a balance having at least a weighing range from 0 to 2 kg and an accuracy of 0.1 g. Balances of this type are available, for example, from Sartorius AG, 37070 Göttingen, Germany. However, it is preferable to use a more accurate balance with an accuracy of 0.1 mg.

Preferably, the substance or capsule(s) can be dispensed or taken up by a metering means which is also weighed by the balance. As a result, any substance which has remained attached to the metering means is always weighed as well and is not recorded as already having been metered in.

Advantageously, the metering head carries all the substance which is to be dispensed with it. Consequently, it does not have to be supplied, for example via flexible hoses, which would have an adverse effect on the weighing accuracy.

In an advantageous exemplary embodiment, the balance is arranged on the tool, and the tool can be detached from and refitted to the tool holder without screws having to be undone.

Preferably, the metering means is arranged on the balance in such a way that the metering means can be detached from and refitted to the balance without screws having to be undone, in particular by being lifted off and put back on. As a result, it is easy to use different types of metering means in order, for example, to meter liquids or solid substances in succession. The handling of the metering means may take place manually or automatically.

Advantageously, the metering means has a metering unit, which comprises a storage vessel, and a drive unit, it being possible for the metering unit to be removed from and refitted to the drive unit without screws having to be undone, in particular by being lifted off and put back on. As a result, it is possible to prepare different substances in a plurality of metering units and then to meter them successively using the same drive unit. The metering units can be handled manually or automatically.

In a variant embodiment which is advantageous for certain tools, the balance bears a vessel for temporarily holding substance which is to be dispensed, which vessel can be completely emptied, the vessel preferably being the concave part of a spoon which can be tilted in order to be completely emptied. This allows substance which is to be dispensed to be weighed accurately in a vessel, which then, depending on the results, is either emptied completely at the metering location, for example into a reaction vessel, i.e. the substance is definitively discharged, or is filled further or, in particular if an excessive quantity of substance has been measured, is emptied at a location other than the metering location and is then refilled.

Advantageously, in addition to the first balance arranged on the tool or on the tool holder, the device according to the invention also has a second balance, the second balance preferably bearing the vessel for temporarily holding substance which is to be dispensed and being used to measure the weight of substance to be dispensed which is being temporarily held, while the first balance can be used also to measure the weight of substance which has not yet been dispensed to the vessel for temporarily holding substance which is to be dispensed. This allows more accurate weight measurement, in particular of substance which is to be dispensed, with the aid of checking measurements carried out by the second balance.

In a preferred exemplary embodiment, the tool holder can rotate about the z direction. This in particular allows the tool to rotate through, for example, 90°, i.e. allows, by way of example, a multi-needle head having a plurality of hollow needles arranged next to one another to be used to meter substances, which may differ according to the hollow needle used, to vessels belonging to a matrix in rows, then allows the multi-needle head to be rotated through 90° and substances, which once again may differ according to the hollow needle used, to be metered to the vessels of the matrix in columns. It is thus possible for a different combination of substances to be metered to each vessel of the matrix in a simple way. Moreover, the rotation allows reaction vessels, starting-material bottles, etc. to be arranged over an area and not just on a straight line.

Preferably, the tool holder can additionally be displaced in a y direction, which is perpendicular to the x direction and the z direction. This enables reaction vessels, starting-material bottles, etc. to be arranged over a larger area.

In an advantageous variant embodiment, the tool is secured to the tool holder by means of magnets, in which case it is preferable, where there are two permanent magnets which attract one another, for one of the two permanent magnets to be arranged on the tool holder and the other of the two permanent magnets to be arranged on the tool, and for it to be possible for the action of the attraction between the two permanent magnets to be cancelled out by means of at least one electromagnet. Connecting tool and tool holder by means of magnets allows automatic securing of the tool to the tool holder, for example by the tool holder being guided over the tool and then lowered onto it or the tool holder being moved laterally onto the tool. Detaching the tool from the tool holder by activating the at least one electromagnet by means of current pulses also contributes to enabling the tool change to take place automatically.

In alternative advantageous variant embodiments, the tool is secured to the tool holder by screw connection, by means of a bayonet connection or by means of a clamping connection, etc. Although these methods of securing are normally more complex to implement, they are relatively simple to automate, in particular if the tool holder can be rotated about the z direction.

Preferably, the tool is a screw metering head, which comprises a screw which can rotate forward and backward about the z direction in a tube which is at least partially open at its lower end and which can be used to take up and dispense substance. A screw metering head of this type can be used for targeted removal of pulverulent or liquid substance from a storage vessel and also for targeted dispensing of this substance.

Advantageously, the lower open end of the tube can be closed off by a diaphragm provided with holes, and there is preferably a ram, which runs on the screw and presses substance through the diaphragm as the screw rotates when substance is being dispensed, arranged in the tube. The use of a diaphragm leads to more uniform dispensing of substance, since the substance is forced uniformly through the holes in the diaphragm. This in turn has the advantage that metering can be carried out more accurately.

Preferably, at the diaphragm there is a stripper which periodically strips off any substance adhering to the diaphragm. This allows more accurate metering.

Advantageously, the tool is a capsule-transporting head, by means of which a capsule can be picked up and released, preferably by suction. A tool of this type makes it possible to transport substances in capsules or similar containers.

Preferably, the tool is a matrix-capsule-transporting head, by means of which capsules which are arranged in the manner of a matrix can be picked up, preferably by suction, and the capsules can be released individually, together or in groups. The matrix-capsule-transporting head also makes it possible to transport substances in capsules, it being possible for a large number of capsules which are arranged in matrix form to be handled at the same time.

Advantageously, the tool is a capsule-handling head, by means of which at least one capsule can be picked up, which capsule can be opened in the tool, preferably by means of a hollow needle, and in which tool the contents of the capsule can preferably be mixed with another substance, in particular a solvent. The mixing can be effected, for example, by adding solvent to the capsule, sucking up substance and solvent from the capsule and returning the material which has been sucked up into the capsule. Alternatively, the hollow needle can also be used to suck substance out of the capsule and dispense it again at another location. The capsule-handling head according to the invention makes it possible to prepare even more successfully for chemical reactions outside a reaction vessel.

In a preferred variant embodiment, the tool is a matrix-capsule-handling head, by means of which a plurality of capsules which are arranged in the form of a matrix can be picked up, which capsules can be opened in the tool, preferably using hollow needles, and in which tool the contents of one capsule can preferably in each case be mixed with another substance, in particular a solvent. The mixing can be effected, for example, by adding solvent to the capsule, sucking up substance and solvent from the capsule and returning the material which has been sucked up into the capsule. Alternatively, the hollow needle can also be used to suck substance out of the capsule and dispense it again at another location. The matrix-capsule-handling head also makes it possible to handle substances in capsules and to prepare for chemical reactions, it being possible for a multiplicity of capsules which are arranged in the form of a matrix to be picked up and processed simultaneously.

In another preferred variant embodiment, the tool is a capsule-dispensing head, in which a multiplicity of capsules are stored and can be dispensed individually, together or in groups, it preferably being possible for the capsules to be opened in the capsule-dispensing head, and it even more preferably being possible for the contents of the capsules to be mixed with another substance, in particular a solvent, in the capsule-dispensing head. The capsule-dispensing head according to the invention makes it possible to prepare for chemical reactions largely outside a reaction vessel and means that the appropriate capsules or the contents thereof simply have to be added to the reaction vessel in order to carry out these chemical reactions.

Advantageously, the tool is a needle head with a hollow needle, a multi-needle head with a plurality of hollow needles, which can preferably be displaced individually in the z direction and/or the distance between which can preferably be adjusted, or a solids-metering head.

Advantageously, the tool is a combination head having at least two identical or different tool parts, one of the tool parts preferably being a needle head, multi-needle head, capsule-transporting head, matrix-capsule-transporting head, capsule-handling head, matrix-capsule-handling head, capsule-dispensing head, screw metering head or solids-metering head. This allows a plurality of method steps to be carried out in succession or simultaneously using a single tool.

Advantageously, the device according to the invention has a camera, which is preferably arranged on the tool holder and which can be used to film an area below the tool holder, as well as a control computer having an image-processing unit, which evaluates images which have been filmed by the camera, it being possible for the displacement of the tool holder and, if necessary, a change of tool to be controlled preferably on the basis of the evaluation result.

In an advantageous variant embodiment, the device according to the invention has an infrared analysis unit, which is preferably arranged on the tool holder and has an infrared transmitter, by means of which infrared waves can be radiated into an area below the tool holder, and an infrared sensor, which can be used to measure reflected infrared waves, as well as a control computer having a measured-value-processing unit, which evaluates the reflected infrared waves measured by the infrared sensor, it preferably being possible for the displacement of the tool holder and, if necessary, a change of tool and/or the quantity of substance to be metered to be controlled on the basis of the evaluation result. The precise way in which an infrared analysis unit of this type functions is described, for example, in U.S. Pat. No. 6,031,233, which is hereby specifically incorporated by reference in the present description.

The camera or the infrared analysis unit, together with the control computer, allows the device to operate completely automatically without an operator having to evaluate the substance or capsule to be handled and then actively control the displacement of the tool holder and/or any change of tool which may be required.

In an advantageous variant embodiment, the device according to the invention comprises a further tool holder for attachment of a further tool which can be displaced in an x direction and in a z direction which is perpendicular to the x direction, it preferably additionally being able to rotate about the z direction and/or to be displaced in a y direction which is perpendicular to the x direction and to the z direction. The second tool holder may be designed and controlled in the same way as the first. With two or even more tool holders with tools attached to them, it is possible to multiply the speed of the device; at the control, it must be ensured that the various tool holders and tools do not impede one another.

A method according to the invention for weighing out a desired quantity of substance using a device having a tool holder, which can be displaced in an x direction and a z direction which is perpendicular to the x direction, and a tool in the form of a metering head, which is secured to the tool holder, and a balance arranged on the tool or on the tool holder, by means of which substance which has been taken up by the tool can be weighed, is characterized by the steps that
a) substance is taken up by the tool;
b) the substance is weighed;
c) the difference between the weighed value obtained and the desired set value is calculated; and
d) if the difference lies outside the range of a desired level of accuracy, the tool is used to discharge substance or take up additional substance depending on this difference;
steps b) to d) being repeated until the difference is equal to zero within the range of a desired level of accuracy.

A similar method according to the invention for dispensing a desired quantity of substance using a device having a tool holder, which can be displaced in an x direction and a z direction which is perpendicular to the x direction, and a tool in the form of a metering head, which is secured to the tool holder, and a balance which is arranged on the tool or on the tool holder and can be used to weigh substance which is to be dispensed from the tool, the balance bearing a vessel for temporarily holding substance which is to be dispensed, which can be completely emptied, is characterized by the steps that
a) a quantity of substance is placed into the vessel for temporarily holding substance which is to be dispensed;
b) the substance in the vessel is weighed;
c) the difference between the weighed value obtained and the desired set value is calculated; and
d) if the difference lies outside the range of a desired level of accuracy, additional substance is added to the vessel or the vessel is at least partially emptied at a location other than an intended metering location and then substance is added to it again, depending on this difference;
steps b) to d) being repeated until the difference is equal to zero within the range of a desired level of accuracy, after which the substance which is present in the vessel is dispensed by the vessel being completely emptied.

A further similar method according to the invention for selecting a capsule with a desired quantity of substance using a device having a tool holder, which can be displaced in an x direction and a z direction which is perpendicular to the x direction, and a tool in the form of a metering head, which is secured to the tool holder, and a balance which is arranged on the tool or on the tool holder and can be used to weigh capsules which have been picked up by the tool, is characterized by the steps that
a) the tool is used to pick up a capsule containing substance;
b) the capsule with substance is weighed;
c) the difference between the weighed value obtained and the desired set value is calculated; and
d) if the difference lies outside the range of a desired level of accuracy, the capsule is released again from the tool and a new capsule containing substance is picked up;
steps b) to d) being repeated until the difference is equal to zero within the range of a desired level of accuracy.

These three weighing methods which operate in accordance with the test principle make it easy to weigh out a desired quantity of substance or a desired object with the desired level of accuracy at any desired location within the area of action of the device. Moreover, for example when substance is being dispensed into, for example, a reaction vessel, a test tube, a substance plate, etc., it is possible for the weight of the quantity of substance which has effectively been dispensed to be measured again. This has two important advantages: 1) Monitoring and more accurate determination of the effective value. 2) If, for example, small quantities of substance remain attached to the tool, this is determined and can be corrected, for example by vibration or topping up the metering.

BRIEF DESCRIPTION OF THE DRAWINGS

The devices according to the invention are described in more detail below with reference to the appended drawings and on the basis of exemplary embodiments. In the drawings:

FIG. 5 shows the tool holder from FIG. 1 with a capsule-transporting head as tool;

FIG. 6 shows the capsule-transporting head from FIG. 5 when it is holding a capsule;

FIG. 7 shows the capsule-transporting head from FIG. 5 when a capsule is being placed in a reaction vessel arranged in a matrix;

FIG. 9 shows a sectional view of a tool in the form of a capsule-handling head with hollow needle;

FIG. 10 shows the capsule-handling head from FIG. 9 on the tool holder from FIG. 1 with a closed capsule which has been picked up;

FIG. 11 shows the capsule-handling head with a capsule which has been picked up as shown in FIG. 10 during the addition of solvent after the capsule has been punctured by the hollow needle;

FIG. 12 shows the capsule-handling head with punctured capsule as shown in FIG. 11 when the capsule, which now contains dissolved substance, is being dispensed;

FIG. 14 shows a sectional view of a tool in the form of a first exemplary embodiment of a capsule-dispensing head having a multiplicity of stored capsules at the tool holder shown in FIG. 1;

FIG. 15 shows a sectional view of a tool in the form of a second exemplary embodiment of a capsule-dispensing head having a multiplicity of stored capsules which can be opened in the capsule-dispensing head, at the tool holder shown in FIG. 1;

FIG. 16 shows the tool holder shown in FIG. 1 with a screw metering head as tool, with a diaphragm which has been pivoted away, in a partially sectional illustration;

FIG. 17 shows the tool holder with screw metering head from FIG. 16 with a diaphragm which has been pivoted under the screw, in a partially sectional view;

DESCRIPTION OF PREFERRED EMBODIMENTS

FIG. 1

Figure 1:
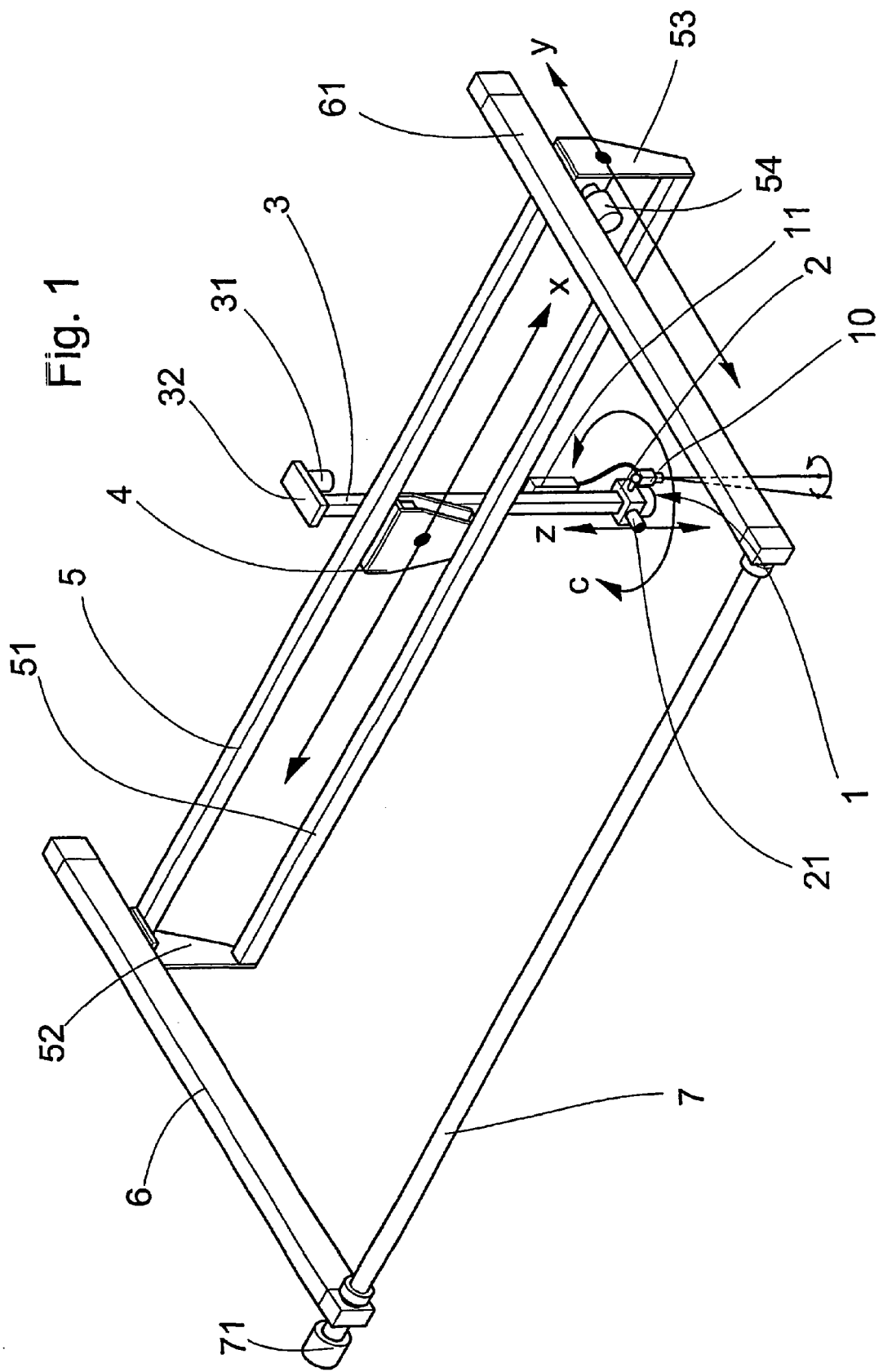
FIG. 1 shows a tool holder which can be displaced in all three spatial directions x, y and z on a linear axis system and can rotate about the z direction.

A linear axis system for holding and displacing a tool holder 1 comprises two guide rails 6, 61, which run parallel to one another in the y direction and are anchored in a fixed position in a manner which is not illustrated. The first ends of the two guide rails 6, 61 are connected by a rotary rod 7, which can be rotated by means of a stepper motor 71. An upper running rail 5 is secured to the two guide rails 6, 61 in such a manner that it can be displaced in the y direction. The upper running rail 5 is fixedly connected to a lower running rail 51 by means of two end plates 52, 53. As a result of the rotary rod 7 being rotated by means of the stepper motor 71, in each case one toothed belt in the interior of the guide rails 6, 61 is driven, causing the running rails 5, 51 to be displaced in the y direction. In the present context, the term displacement in the y direction is to be understood as meaning both a displacement in the +y direction and in the −y direction (the opposite direction).

A carriage 4 is secured to the two running rails 5, 51 in such a manner that it can be moved in the x direction. In the present context, the term movement in the x direction is once again to be understood as meaning both a movement in the +x direction and in the −x direction (the opposite direction). The carriage 4 is driven by a stepper motor 54 via a toothed belt arranged in the hollow upper guide rail 5.

A tool rod 3 is secured to the carriage 4 in such a manner that it can move in the z direction. In the present context, the term movement in the z direction is once again to be understood as meaning both a movement in the +z direction and in the −z direction (the opposite direction). In order for the tool rod 3 to be displaced, a stepper motor 31 is attached to it via a hollow plate 32, and a toothed belt is arranged in the hollow plate 32 and the tool rod 3.

At the lower end of the tool rod 3 there is a rotary drive 2, to which the tool holder 1 is secured. The tool holder 1 can be rotated both ways about the z direction, as indicated by the arrow c, with the aid of a rotary motor 21. In order to secure a tool, the tool holder 1 substantially consists of a permanent magnet, in which an electromagnet is arranged.

A camera 10, which is directed downward in the z direction and can be used to film an area below the tool holder 1, is attached to the tool holder 1. The images which are filmed by the camera 10 are transmitted via a data line to an image-processing unit of a control computer 11, which evaluates these images. The control computer 11 can then control the displacement of the tool holder 1 in the x, y, z and c directions by means of the motors 54, 71, 31 and 21 and the selection, securing or release of a tool on the basis of the evaluation results.

The following consideration applies to the whole of the remainder of the description. If a figure includes reference symbols which are provided for the purpose of clarity of the drawing but these reference symbols are not mentioned in the immediately associated text of the description, or vice versa, reference is made to the corresponding explanations given in preceding descriptions of figures.

FIG. 2

In this case, a needle head 100 is removably secured as the tool to the holder 1 by means of a permanent magnet 101. The permanent magnet 101 of the needle head 100 and the permanent magnet of the tool holder 1 attract one another, so that when the needle head 100 is removed it can be secured to the tool holder 1 by being placed onto the latter, an operation which can be performed automatically, i.e. the needle head 100 does not have to be attached to the tool holder 1 manually. The needle head 100 is detached from the tool holder 1 by means of the electromagnet which is arranged in the tool holder 1, cannot be seen and, when it receives a current pulse, cancels out the action of the attraction between the permanent magnet 101 of the needle head 100 and the permanent magnet of the tool holder 1.

A linear drive 103 is attached to the permanent magnet 101 via a plate 102. A hollow needle 105 is secured to the outer cylinder of the linear drive 103 by means of two holding parts 104, which are provided with continuous receiving holes for the hollow needle 105. With the aid of the linear drive 103, the hollow needle 105 can be displaced in the z direction.

A hollow needle 105 of this type can be used, for example, to meter or remove liquid substances into or from reaction vessels. In particular, for this purpose a suction and/or blowing means can be connected to the top end of the hollow needle 105.

Unlike in FIG. 1, a balance 9, which can be used to measure the total weight of the tool holder 1, the needle head 100 and the substance which is present in the hollow needle 105, is additionally arranged on the tool holder 1 below the rotary drive 2. If the weight of the tool holder 1 and the needle head 100 is subtracted from this total weight, the result is the weight of the substance which is present in the hollow needle 105. The weight of substance which has been taken up or dispensed can be determined by differential measurements.

Figure 3:
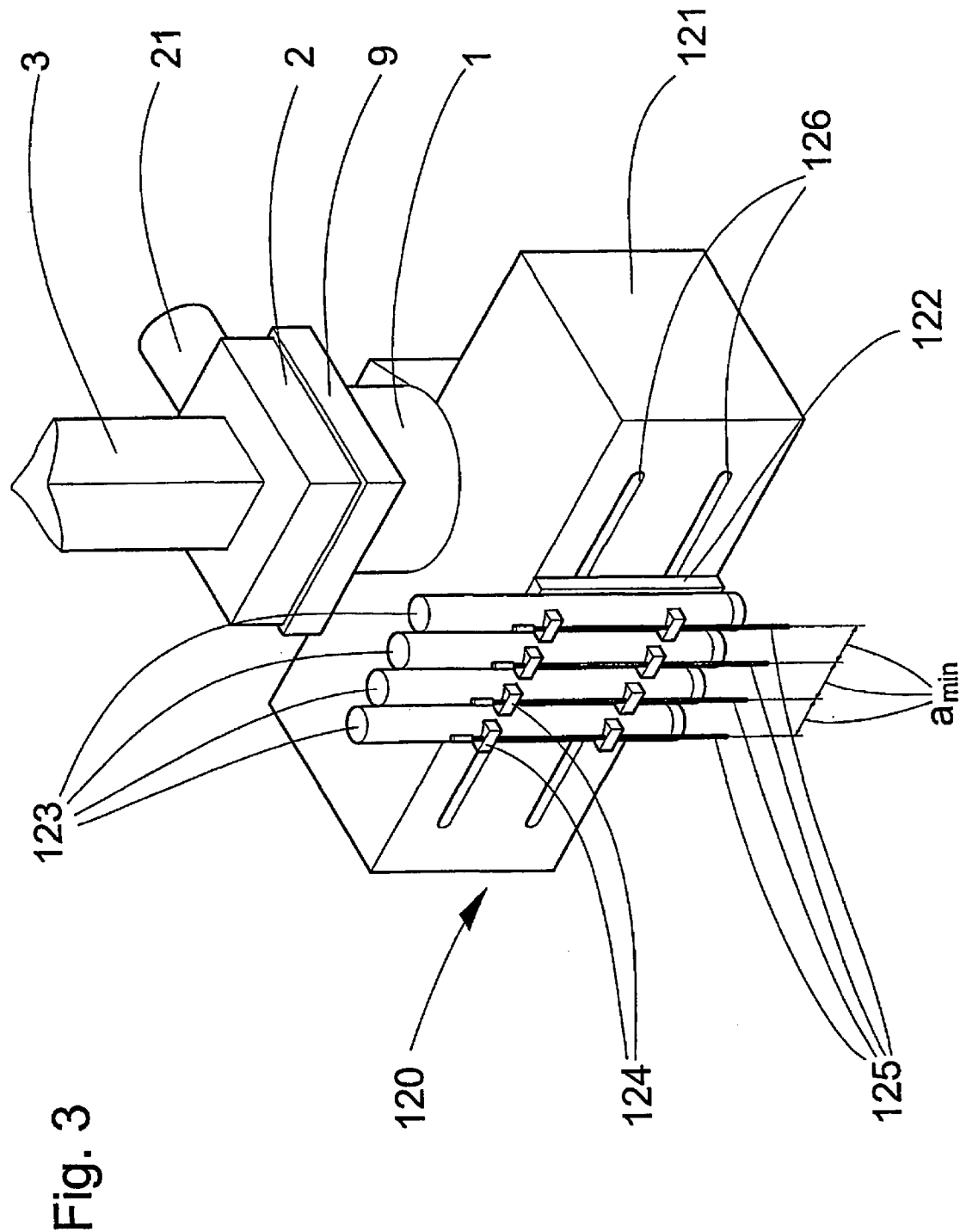
FIG. 3 shows the tool holder from FIG. 1, but additionally with a balance arranged thereon, having a needle head with four hollow needles which can be displaced with respect to one another as tool, the four hollow needles being at a minimum distance from one another.
Figure 4:
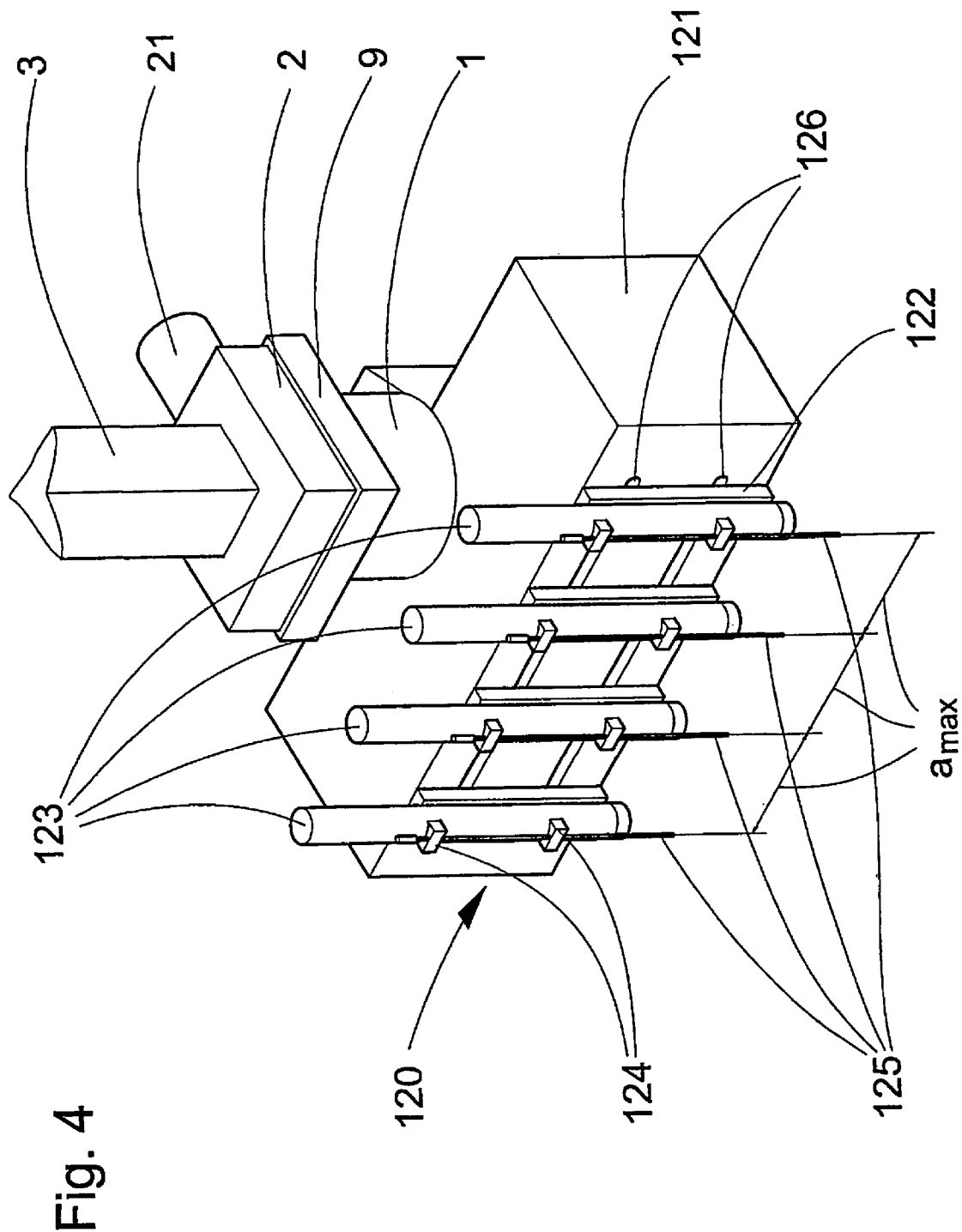
FIG. 4 shows the tool holder with needle head from FIG. 3, with the four hollow needles at a maximum distance from one another.
Figure 8:
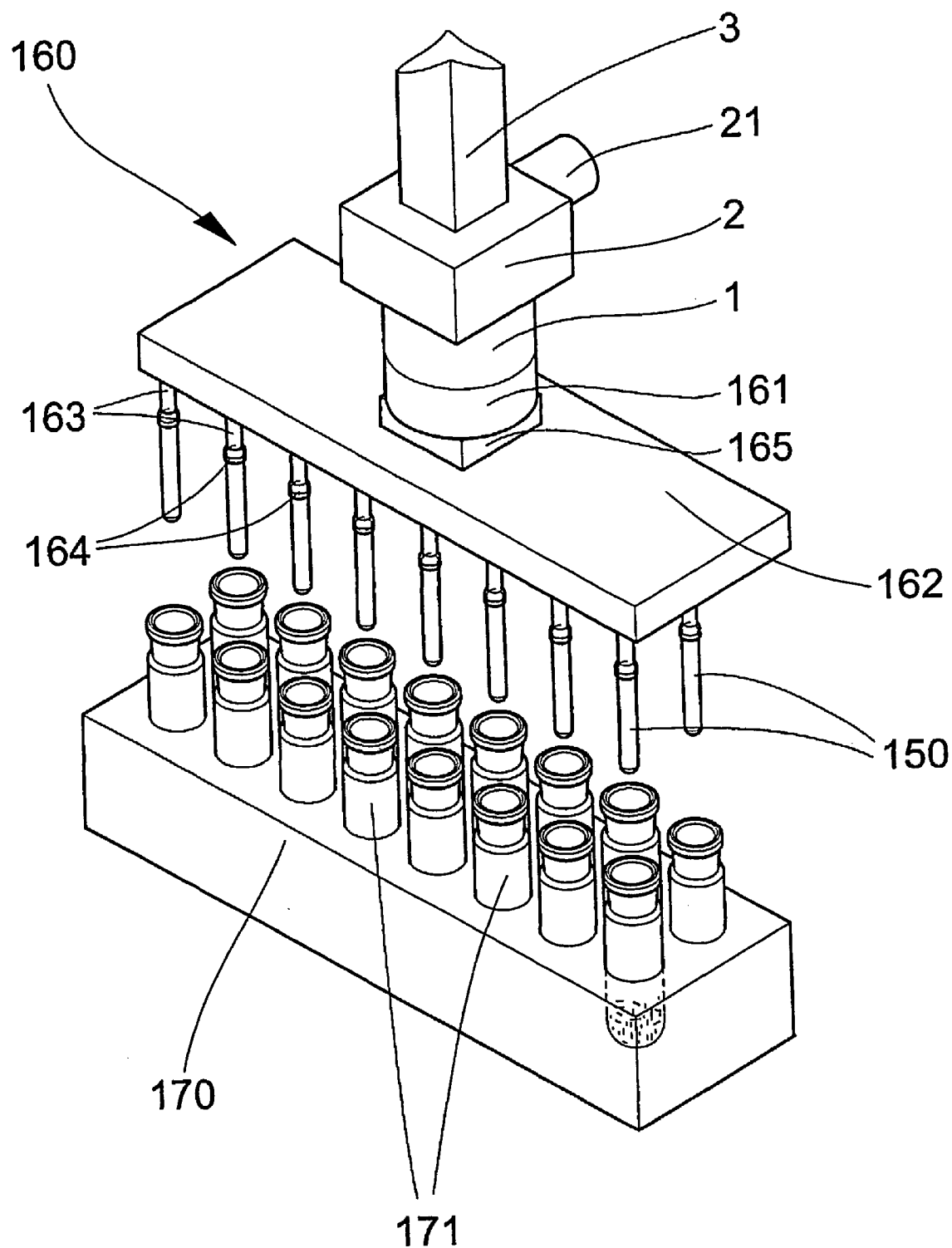
FIG. 8 shows the tool holder from FIG. 1 with a matrix-capsule-transporting head as tool.
Figure 13:
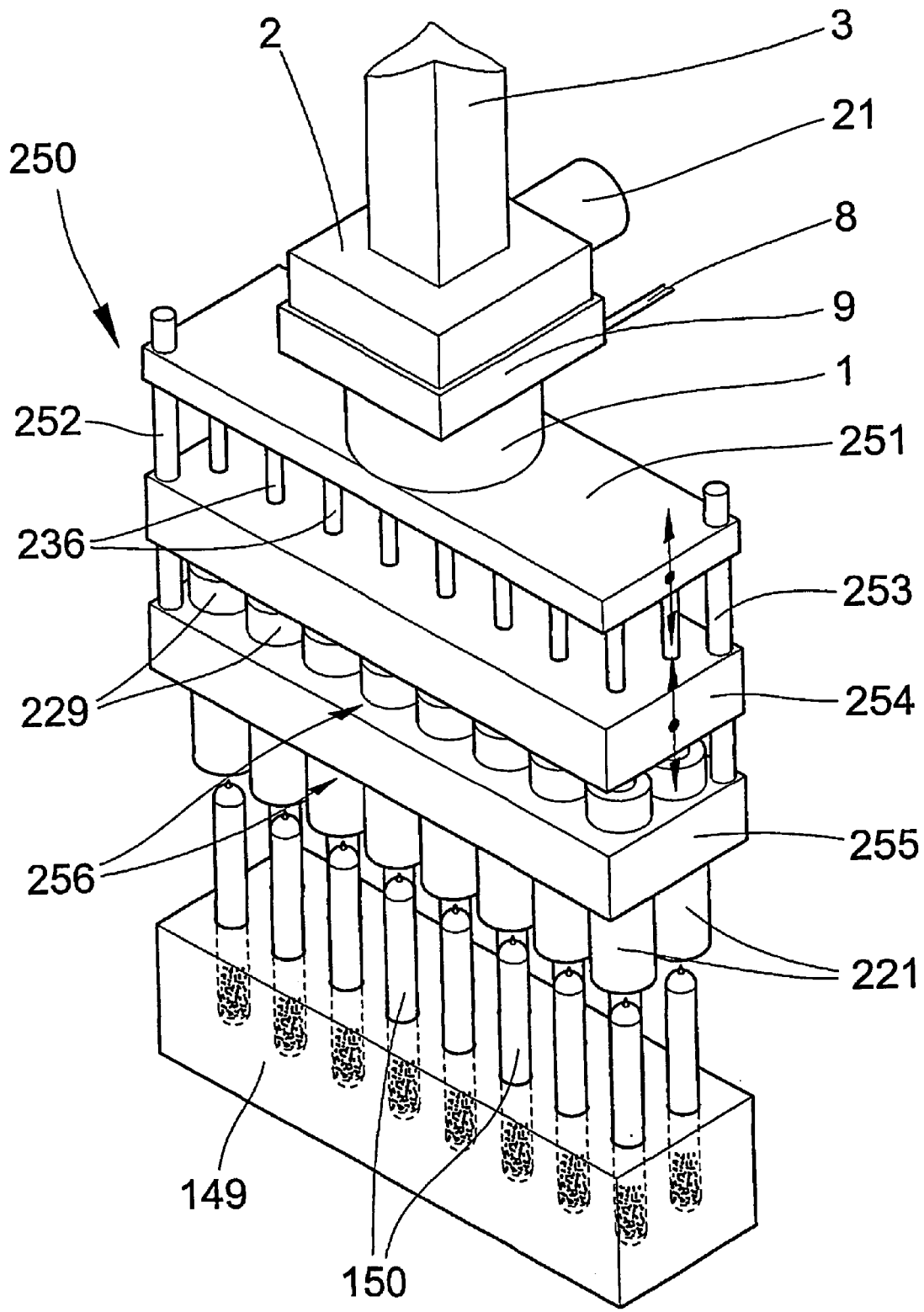
FIG. 13 shows the tool holder from FIG. 1, but additionally with a balance arranged thereon, with a diagrammatically depicted matrix-capsule-handling head as tool and capsules arranged in a matrix.
Figure 18:
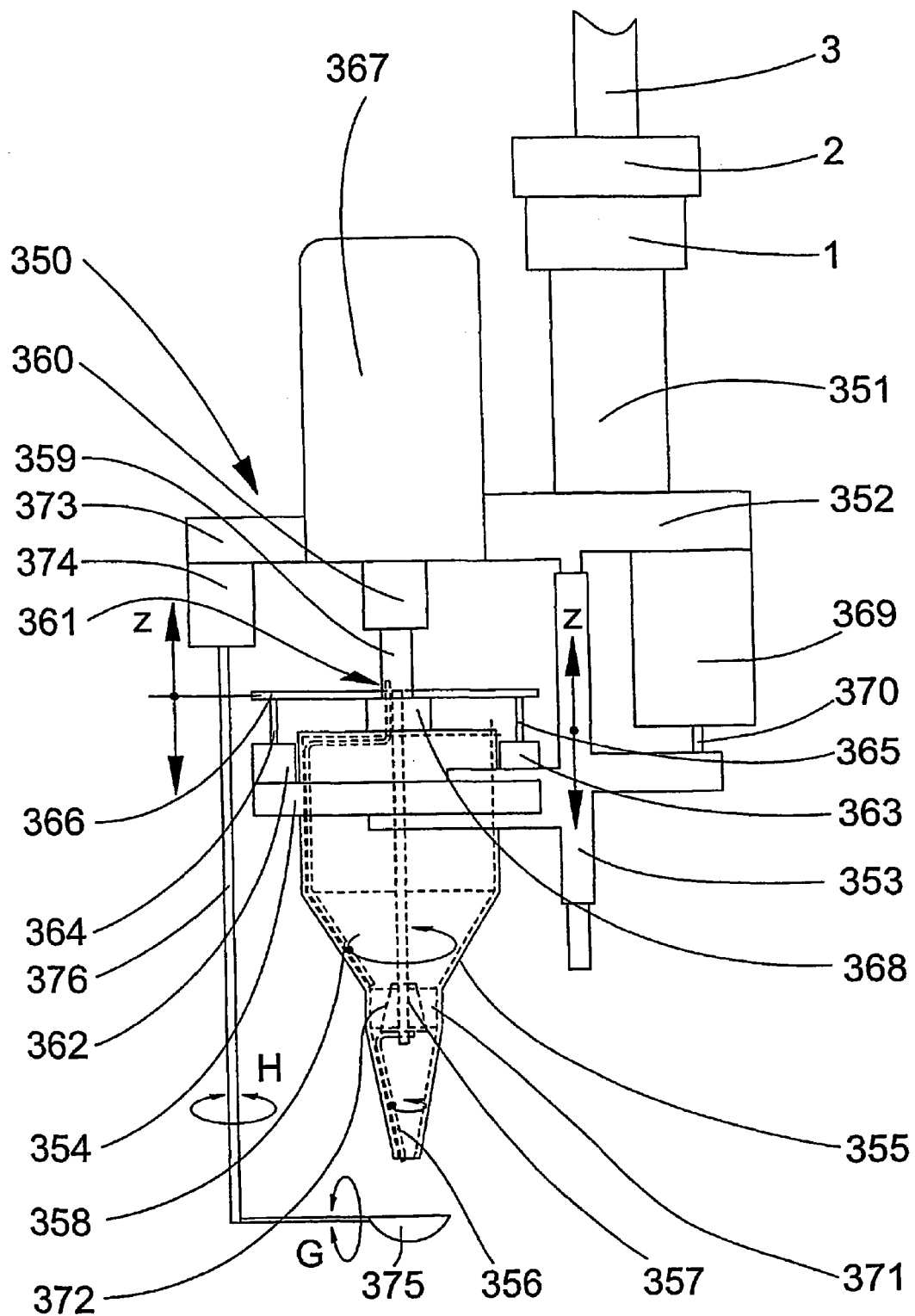
FIG. 18 shows the tool holder from FIG. 1 with a solids-metering head as tool.

FIGS. 3 and 4

Figure 2:
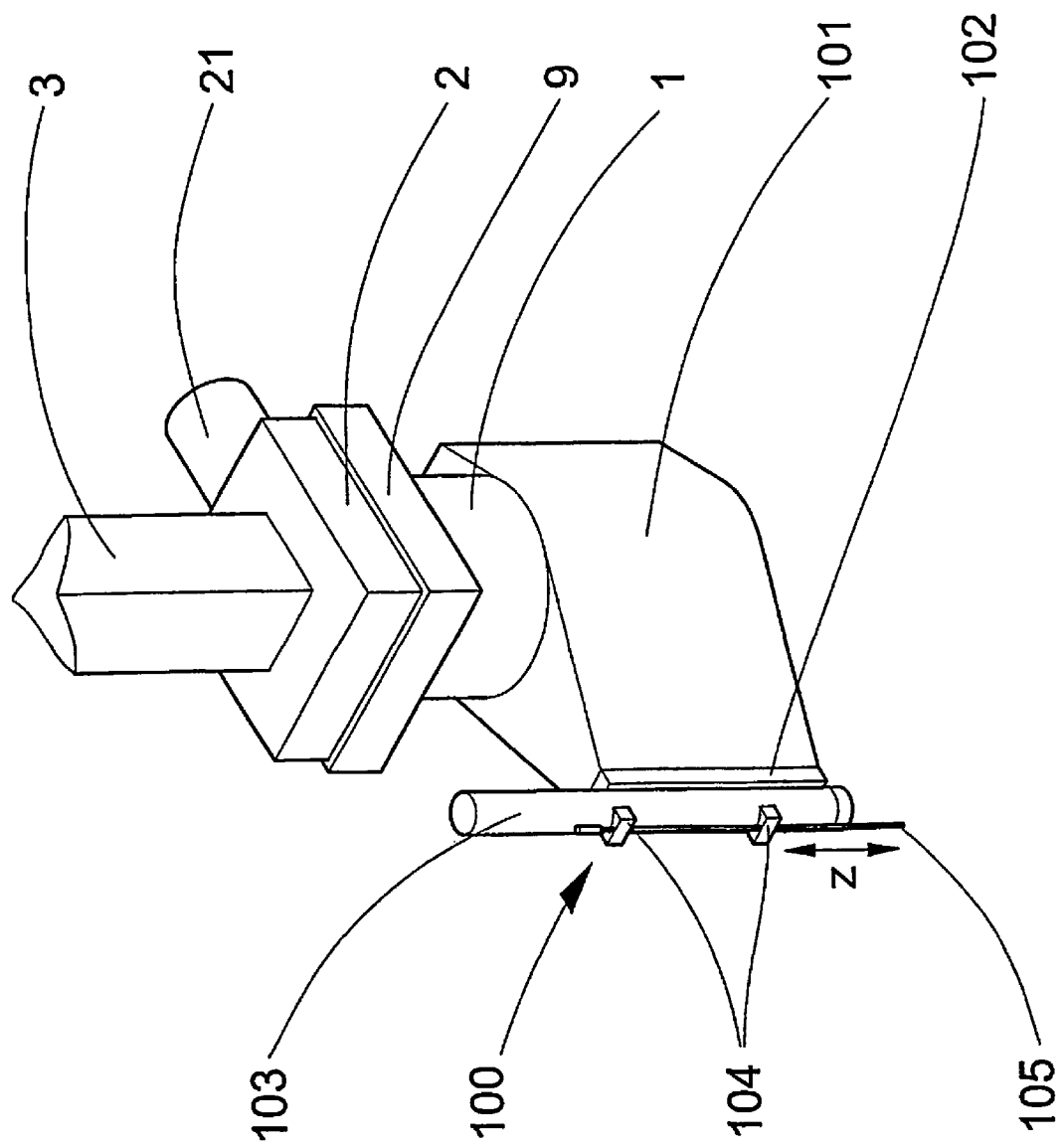
FIG. 2 shows the tool holder from FIG. 1, but additionally with a balance arranged thereon, having a needle head with a hollow needle as tool.

The tool is in this case formed by a needle head 120 with four hollow needles 125, which can be individually displaced in the z direction and the distance between which can be adjusted from a minimum distance $a_{min}$ to a maximum distance $a_{max}$, the distance between each pair of adjacent hollow needles 125 always being identical. To this end, the hollow needles 125 are each secured to the outer cylinder of a linear drive 123 by means of two holding parts 124 which are provided with continuous hollow-needle receiving holes. The linear drives 123 which can be used to displace the hollow needles 125 individually in the z direction are for their part in each case attached to an associated plate 122. The four plates 122 are arranged movably in two grooves in a permanent magnet 121, the drive for this purpose being effected by means of two spindles which are driven by a motor and are located inside the permanent magnet 121. The needle head 120, as described in connection with FIG. 2, is connected to the tool holder 1 via the permanent magnet 121. Once again, the needle head 120 is detached from the tool holder 1 by means of the electromagnet (not visible) arranged in the tool holder 1.

A needle head 120 of this type can be used, for example, to meter liquid to or remove liquid from a plurality of reaction vessels simultaneously. In particular, suction and/or blowing devices can be connected to the top end of the hollow needles 125 for this purpose.

Unlike in FIG. 1, a balance 9, which can be used to measure the total weight of the tool holder 1, the needle head 120 and the substance which is present in the hollow needles 125, is additionally arranged on the tool holder 1 below the rotary drive 2. If the weight of the tool holder 1 and of the needle head 120 is subtracted from this total weight, the result is the weight of the substances which are present in the hollow needles 125. The weight of substances which have been taken up or dispensed can be determined by means of differential measurements.

FIGS. 5 to 7

The tool is in this case formed by a capsule-transporting head 140, by means of which a tightly closed capsule 150, which is in the form of a small tube and contains a pulverulent substance 151, can be picked up by suction. The capsule-transporting head 140 comprises a permanent magnet 141, by means of which, as described in a corresponding way in connection with FIG. 2, it is connected to the tool holder 1. It can be released by means of the electromagnet arranged in the tool holder 1. A suction tube 143 having a capsule-holding end piece 144 is attached to the permanent magnet 141 via a balance 145 and an intermediate part 142. A reduced pressure can be generated in the suction tube 143 by means of a conventional suction means (not shown).

To pick up a capsule 150, the capsule-transporting head 140 is moved such that the capsule-holding end piece 144 is above the top end of the capsule 150, and then the capsule 150 is picked up as a result of a reduced pressure being generated in the suction tube 143, as illustrated in FIG. 6. Then, the capsule 150 is transported by the linear axis system to the intended location, in FIG. 7 a reaction vessel 171 arranged in a matrix 170, where it is released into the reaction vessel 171 as a result of the reduced pressure in the suction tube 143 being eliminated.

The balance 145 can be used to measure the total weight of the intermediate part 142, the suction tube 143 with the capsule-holding end piece 144 and the capsule 150 filled with substance 151 which it has picked up. If the weight of the intermediate part 142 and the suction tube 143 with the capsule-holding end piece 144 are subtracted from this total weight, the result is the weight of the capsule 150 filled with substance 151. The weight of the substance 151 in the capsule 150 can be determined by differential measurements using an empty capsule 150.

FIG. 8

The tool is in this case formed by a matrix-capsule-transporting head 160 which comprises a permanent magnet 161, by means of which, as has been described in a corresponding way in connection with FIG. 2, it is connected to the tool holder 1. It is released by means of the electromagnet arranged in the tool holder 1. Sixteen suction tubes 163, which are arranged in the form of a matrix and each have a capsule-holding end piece 164, are attached to the permanent magnet 161 via a balance 165 and a suction-tube plate 162. A reduced pressure can be generated in the suction tubes 163 via the suction-tube plate 162 by means of a conventional suction means (not shown).

To pick up capsules 150, the matrix-capsule-transporting head 160 is moved such that the capsule-holding end pieces 164 are above the top ends of the capsules 150, and then the capsules 150 are picked up as a result of a reduced pressure being generated in the suction tubes 163. Then, the capsules 150 are transported by the linear axis system to the intended location, in this case reaction vessels 171 arranged in a matrix 170, where the capsules 150 are dispensed into the reaction vessels 171 as a result of the reduced pressure in the suction tubes 163 being eliminated.

The balance 165 can be used to measure the total weight of the suction tube plate 162, the suction tubes 163 with the capsule-holding end piece 164 and the capsules 150 filled with substances which they have picked up. If the weight of the suction tube plate 162 and the suction tubes 163 with the capsule-holding end pieces 164 is subtracted from this total weight, the result is the weight of the capsules 150 filled with substances. The weight of the substances in the capsules 150 can be determined by differential measurements using empty capsules 150.

FIGS. 9 to 12

In this case, the tool is formed by a capsule-handling head 220, which comprises a cylindrical housing 221 which is divided into two compartments 223 and 224 by a partition 222 and is closed off at the top by an end wall 227. At the open end of the bottom compartment 223, in the cylindrical housing 221, there is an air-filled sleeve 225, for example made from rubber, which in the unladen state as shown in FIG. 9 has an internal diameter $d_{min}$. In the upper compartment 224 there is a plunger 226, to which a plunger rod 228, which projects out through the end wall 227 and is provided at its top end with an outer push-button 229, is attached. Between the plunger 226 and the cylindrical housing 221 and between the plunger rod 228 and the end wall 227 there is in each case an annular seal 230, 231. Between the plunger 226 and the partition 222 there is a coil spring 232, which in the unladen state holds the plunger 226 in the position shown in FIG. 9. Between the plunger 226 and the end wall 227 there is an air-filled space 233, which is in communication with the interior of the sleeve 225 via an air line 234.

In addition, the capsule-handling head 220 comprises a hollow needle 235, to which an inner push-button 236 is attached. The inner push-button 236 is mounted movably in a recess 237 in the outer push-button 229, a coil spring 238 being arranged in the recess 237 below the inner push-button 236, which coil spring 238, in the unladen state, holds the inner push-button 236 and the hollow needle 235 in the position shown in FIG. 9. The hollow needle 235 passes through the plunger rod 228, the plunger 226 and the partition 222. It is in communication with the internally hollow inner push-button 236, which can be fed, for example, with a solvent or another liquid via a feed line 239.

FIG. 10 shows the capsule-handling head 220 after it has picked up a capsule 150, an operation which can be effected by placing the capsule-handling head 220 onto the capsule 150. The capsule 150 is held by the sleeve 225, which now has an internal diameter d which corresponds to the external diameter of the capsule 150 and is greater than the internal diameter $d_{min}$ in the stress-free state.

FIG. 10 also illustrates that the capsule-handling head 220 comprises a balance 241 and a permanent magnet 240, via which, as described in a corresponding way in connection with FIG. 2, it is connected to the tool holder 1. The capsule-handling head 220 is detached from the tool holder 1 by means of the electromagnet arranged in the tool holder 1. Moreover, the figure diagrammatically indicates that the inner push-button 236 can be actuated by a rotary lever 242 and the outer push-button 229 can be actuated by a rotary lever 244, the two rotary levers 242, 244 being articulatedly mounted on a rod 243, which is secured to the balance 241 by means of a bearing part 245, in such a manner that they can rotate in the direction indicated by the arrows. The drives for the two rotary levers 242, 244, which are controlled by the control computer, are not shown. FIGS. 9, 11 and 12 do not show the permanent magnet 240, the balance 241, the two rotary levers 242, 244, the rod 243, the bearing part 245 and the tool holder 1, for reasons of clarity.

The balance 241 can be used to measure the total weight of the capsule 150 which has been picked up by the capsule-handling head 220 and is filled with substance and of the capsule-handling head 220 with the exception of the permanent magnet 240 and the balance 241 itself. If the weight of the capsule-handling head 220 with the exception of the permanent magnet 240 and the balance 241 is subtracted from this total weight, the result is the weight of the capsule 150 filled with substance. The weight of the substance in the capsule 150 can be determined by differential measurements using an empty capsule 150.

The coil spring 238 is compressed as a result of the inner push-button 236 being pushed downward, and as a result the hollow needle 235 is forced into the capsule 150, as illustrated in FIG. 11. As a result, the capsule 150 is opened and it can be supplied, via the hollow needle 235, with a substance from the inner push-button 236, which is fed via the feed line 239. Alternatively, the feed line 239 could also be connected directly to the hollow needle 235. The substance supplied, in particular a solvent, can be mixed with the substance which is already present in the capsule 150, for example by the capsule-handling head 220 being shaken. If a sufficiently long hollow needle is used, the mixing could also be effected by the substances which are present in the capsule 150 being sucked up and discharged again a number of times.

If pressure is no longer being exerted on the inner push-button 236, the coil spring 238 forces it back upward into the starting position.

In order for the capsule 150 to be released, the outer push-button 229 is pressed downward, as illustrated in FIG. 12. In the process, the plunger rod 228 and the plunger 226 are moved downward so as to compress the coil spring 232, with the result that the size of the space 233 between the plunger 226 and the end wall 227 is increased greatly and a reduced pressure is generated therein. This reduced pressure causes air to be extracted from the interior of the sleeve 225 via the air line 234, with the result that the internal diameter of the sleeve 225 is increased to a maximum value $d_{max}$, which is greater than the external diameter of the capsule 150, so that the capsule 150 is no longer held by the sleeve 225 and drops downward under the force of gravity.

If pressure is no longer being exerted on the outer push-button 239, the coil spring 232 forces it back upward into the starting position shown in FIG. 9.

FIG. 13

The tool is in this case formed by a matrix-capsule-handling head 250, which comprises a holding plate 255 which is removably connected to the tool holder 1 by means of a permanent magnet, in a manner which is not illustrated. The matrix-capsule-handling head 250 is detached from the tool holder 1 by means of the electromagnet which is arranged in the tool holder 1 and the power supply line 8 of which can be seen. Two rods 252, 253, which are fixedly connected to the holding plate 255, extend upward in the z direction, i.e. vertically, from two diagonally opposite corner regions of the holding plate 255. A release plate 254, which can be displaced in the z direction and is guided by the rods 252, 253 in two diagonally opposite corner regions, is arranged above the holding plate 255. A trigger plate 251 located above the release plate 254 can likewise be displaced in the z direction and is guided by the two rods 252, 253. The vertical displacement of the release plate 254 and of the trigger plate 251 is effected by two motors (not shown), although in principle it could also be brought about manually.

Sixteen capsule-handling elements 256 are secured in the holding plate 255. The capsule-handling elements 256, which are only diagrammatically depicted in this figure, apart from the connecting part 241 and the permanent magnet 240, are constructed in substantially the same way as the capsule-handling heads 220 shown in FIGS. 9 to 12 and each comprise, in addition to a cylindrical housing 221, an outer push-button 229 and an inner push-button 236. The inner push-buttons 236 with the hollow needles attached to them can be actuated jointly as a result of the trigger plate 251 being lowered. The joint actuation of, the outer push-buttons 229 is effected as a result of the release plate 254 being lowered. The matrix-capsule-handling head 250 can be used to take hold of sixteen capsules 150 arranged in a matrix 149 together, to open each of them by means of a hollow needle 235 and if appropriate to mix the substances contained therein with other substances and release them again.

Unlike in FIG. 1, a balance 9, which can be used to measure the total weight of the tool holder 1, the matrix-capsule-handling head 250 and the capsules 150, which have been picked up by it and are filled with substances, is additionally arranged on the tool holder 1 beneath the rotary drive 2. If the weight of the tool holder 1 and of the matrix-capsule-handling head 250 is subtracted from this total weight, the result is the weight of the capsules 150 filled with substances. The weight of the substances in the capsules 150 can be determined by means of differential measurements using empty capsules.

FIG. 14

The tool is in this case a first exemplary embodiment of a capsule-dispensing head 280, which comprises a balance 296 and a permanent magnet 295, by means of which, as has been described in a corresponding way in connection with FIG. 2, it is connected to the tool holder 1. The removal of the capsule-dispensing head 280 from the tool holder 1 is effected by means of the electromagnet arranged in the tool holder 1.

The capsule-dispensing head 280 comprises a substantially cylindrical housing 281, the lower part of which narrows to form a neck 282 and in which a large number of capsules 150, which each contain a substance 151, are stored. One of the capsules 150 is held by an air-filled sleeve 283, which is arranged in the neck 282 and is made, for example, from rubber. In a separate cylinder 284 there is a plunger 285, to which a plunger rod 286, which projects out through an end wall 287 of the cylinder 284 and is provided at its top end with a push-button 288, is attached. Between the plunger 285 and the cylinder 284 and between the plunger rod 286 and the end wall 287 there is in each case an annular seal 289, 290. Between the plunger 285 and the base 291 of the cylinder 284 there is a coil spring 292, which in the stress-free state holds the plunger 285 in the position illustrated. Between the plunger 285 and the end wall 287 there is an air-filled space 293, which is in communication with the interior of the sleeve 283 via an air line 294.

In order for the capsule 150 which is being held by the sleeve 283 to be released, the push-button 288 is pressed downward. In the process, the plunger rod 286 and the plunger 285 are moved downward so as to compress the coil spring 292 with the result that the size of the space 293 between the plunger 285 and the end wall 287 is increased greatly and a reduced pressure is generated therein. This reduced pressure causes air to be extracted from the interior of the sleeve 283 via the air line 294, with the result that the internal diameter of the sleeve 283 is increased to a value which is greater than the external diameter of the capsule 150, so that the capsule 150 is no longer held by the sleeve 283 and drops downward under the force of gravity. At the same time, a second capsule 150 moves up to take the place of the first capsule 150, it being important for the pressure on the push-button 288 to be released again sufficiently quickly, so that the coil spring 292 moves the plunger 285 back upward into the starting position, the size of the space 293 is reduced again and air is fed back to the sleeve 283 via the air line 294 sufficiently quickly for the capsule 150 to be gripped by the sleeve 283.

Moreover, the figure diagrammatically indicates that the push-button 288 can be actuated by a rotary lever 297, the rotary lever 297 being articulatedly mounted on a rod 298 in such a manner that it can rotate in the direction of the arrow, this rod in turn being secured to the balance 296 by means of a bearing part 299. The drive of the rotary lever 297, which is controlled by the control computer, is not illustrated.

The balance 296 can be used to measure the total weight of the capsules 150 which are present in the capsule-dispensing head 280 and are filled with substances and of the capsule-dispensing head 280, with the exception of the permanent magnet 295 and the balance 296 itself. The weight of a capsule 150 filled with substance can be measured by measuring the weight difference before and after a capsule 150 has been dispensed. The weight of the substance in the capsule 150 can be determined by differential measurements using an empty capsule 150.

FIG. 15

The tool is in this case a second exemplary embodiment of a capsule-dispensing head 300, which comprises a balance 318 and a permanent magnet 317, by means of which, as has been described in a corresponding way in connection with FIG. 2, it is connected to the tool holder 1. The removal of the capsule-dispensing head 300 from the tool holder 1 is effected by means of the electromagnet arranged in the tool holder 1.

The capsule-dispensing head 300 comprises a substantially cylindrical housing 301, which in its lower part narrows to form a neck 302 and in which a multiplicity of capsules 150, which each contain a substance 151, are stored. One of the capsules 150 is held by an air-filled sleeve 303, which is arranged in the neck 302 and is made, for example, from rubber, while the other capsules 150 are arranged in the cylindrical housing 301 in a chamber part 315 which can rotate in the manner of a revolver as indicated by arrow E. In a separate cylinder 304 there is a plunger 305, to which a plunger rod 306, which projects out through an end wall 307 of the cylinder 304 and is provided at its top end with a push-button 308, is attached. Between the plunger 305 and the cylinder 304 and between the plunger rod 306 and the end wall 307 there is in each case an annular seal 309, 310. Between the plunger 305 and the base 311 of the cylinder 304 there is a coil spring 312, which in the stress-free state holds the plunger 305 in the position illustrated. Between the plunger 305 and the end wall 307 there is an air-filled space 313, which is in communication with the interior of the sleeve 303 via an air line 314.

In addition, the capsule-dispensing head 300 comprises a hollow needle 316, which passes through the push-button 308, the plunger rod 306, the plunger 305 and the base 311. As a result of the hollow needle 316 being forced downward, the capsule 150 which is located above the capsule which is held by the sleeve 303 can be punctured. If necessary, another substance, in particular a solvent, can be fed to the open capsule 150 via the hollow needle 316.

In order for the capsule 150 which is being held by the sleeve 303 to be released, the push-button 308 is pushed downward. In the process, the plunger rod 306 and the plunger 305 are moved downward so as to compress the coil spring 312, with the result that the size of the space 313 between the plunger 305 and the end wall 307 is increased greatly and a reduced pressure is generated therein. This reduced pressure causes air to be extracted from the interior of the sleeve 303 via the air line 314, with the result that the internal diameter of the sleeve 303 is increased to a value which is greater than the external diameter of the capsule 150, so that the capsule 150 is no longer held by the sleeve 303 and drops downward under the force of gravity. At the same time, the capsule located above this capsule 150 drops into the position which was occupied by the capsule 150 which has been released, it being important for the pressure on the push-button 308 to be released again sufficiently quickly, so that the coil spring 312 moves the plunger 305 back upward into the starting position, the size of the space 313 is reduced again and air is fed back to the sleeve 303 via the air line 314 sufficiently quickly for the next capsule 150 to be gripped by the sleeve 303. Then, the chamber part 315 is rotated one step onward, so that a new capsule 150 moves into the position directly above the neck 302. The rotation of the chamber part 315 may be effected externally, for example by hand, or may be triggered by the actuation of the push-button 308. For this purpose, if necessary the cylindrical housing 301 has access openings.

Moreover, the figure diagrammatically indicates that the hollow needle 316 can be actuated by a rotary lever 319 and the push-button 308 can be actuated by a rotary lever 322, the two rotary levers 319, 322 being articulatedly mounted on a rod 321, which is secured to the balance 318 by means of a bearing part 323, in such a manner that they can rotate in the direction indicated by the arrows. The drives of the two rotary levers 319, 322, which are controlled by the control computer, are not shown.

A cuboidal housing, in which the capsules 150 are arranged in a plate which can be moved in the x direction and in the y direction, may also be provided instead of the cylindrical housing 301 and the chamber part 315 which can rotate in the manner of a revolver.

The balance 318 can be used to measure the total weight of the capsules 150 which are filled with substance and are present in the capsule-dispensing head 300 and of the capsule-dispensing head 300 with the exception of the permanent magnet 317 and the balance 318 itself. The weight of a capsule 150 filled with substance can be measured by measuring the weight difference before and after a capsule 150 has been dispensed. The weight of the substance in the capsule 150 can be determined by differential measurements using an empty capsule 150.

FIGS. 16 and 17

The tool is in this case formed by a screw metering head 320, which comprises a permanent magnet 321, by means of which, as has been described in a corresponding way in connection with FIG. 2, it is connected to the tool holder 1. The removal of the screw metering head 320 from the tool holder 1 is effected by means of the electromagnet arranged in the tool holder 1.

A motor part 326 is attached to the permanent magnet 321 by means of a balance 333 and a connecting part 322, and an open tube 323, in which a screw 324, which can rotate forward and backward about the z direction as indicated by arrow F, with screw shaft 325 is mounted at its bottom end. The screw 324 is anchored by means of the screw shaft 325 in such a manner that it can be rotated by a motor arranged in the motor part 326 and is stable in the z direction. Rotation of the screw 324 results in a ram 327 which runs on the screw moving up or down. The lower, open end of the tube 323 can be closed off by means of a diaphragm 328 which is provided with holes 329 and is secured to two pivot arms 330, 331 which are mounted pivotably in a suspension 332 on the motor part 326. In FIG. 16, the diaphragm 328 has been removed from the open end of the tube 323 and can be moved into the closed position illustrated in FIG. 17 by being pivoted in the direction indicated by arrow I.

To take up substance, the open end of the tube 323 is moved onto the substance with the diaphragm 328 in its pivoted-away position. Rotation of the screw 324 in the direction which moves the ram 327 upward causes substance to be carried upward directly by the screw 324.

To dispense substance, the diaphragm 328 is pivoted under the screw 324 to cover the open end of the tube 323. Then, the screw 324 is rotated in the direction which moves the ram 327 downward, with the result that substance is forced out downward through the holes 329 in the diaphragm 328 on the one hand directly by the screw 324 and on the other hand by means of the ram 327. A stripper 334, in the shape of a U-shaped wire, part of which bears against the underside of the diaphragm 328, is, like the two pivot arms 330, 331, mounted pivotably on the suspension 332. Pivoting the stripper 334 in the direction indicated by the arrow K ensures that any substance which has remained attached to the bottom of the diaphragm 328 is periodically stripped off, allowing more accurate metering.

The diaphragm 328 is responsible for continuous delivery of substance, but in principle metering is also possible without a diaphragm 328.

The balance 333 can be used to measure the total weight of the substance which has been taken up by the screw 324 and of the screw metering head 320 with the exception of the permanent magnet 321 and the balance 333 itself. If the weight of the screw metering head 320 with the exception of the permanent magnet 321 and the balance 333 itself is subtracted from this total weight, the result is the weight of the substance which has been taken up. The weight of substance which has been additionally taken up or dispensed can be determined by differential measurements.

FIG. 18

The tool is in this case formed by a solids-metering head 350, which comprises a permanent magnet 351, by means of which, as has been described correspondingly in connection with FIG. 2, it is connected to the tool holder 1. The removal of the solids-metering head 350 from the tool holder 1 is effected by means of the electromagnet arranged in the tool holder 1.

On the permanent magnet 351 there is a bearing part 352, on which a carriage 353 is mounted in such a manner that it can move in the z direction. A holding plate 354 has been pushed laterally into the carriage 353 and has attached to it a metering housing 355, the internal diameter of which decreases in steps toward the bottom and which has an intermediate base 371 with a conical metering opening which tapers upward. The holding plate 354 with the metering housing 355 can be detached from the carriage 353 by means of a horizontal movement involving little force.

A rotating metering shaft 357, which drives a stripper 356 and can be displaced in the z direction, runs in the z direction centrally through the metering housing 355 and the conical metering opening in the intermediate base 371. At the lower end of the metering shaft 357 there is a closure cone 372 which tapers upward and partially or completely closes off the conical metering opening in the intermediate base 371 depending on the z position, substance which flows downward when the metering opening is partially open being fed to the stripper 356.

The rotating metering shaft 357 is fixedly connected to a co-rotating bearing part 368, projects from below into a shaft 359 driven by a motor 360 and is rotated with the shaft 359. A rotating stripper 358 which is arranged in the upper part of the metering housing 355 runs through the bearing part 368 and likewise projects into the shaft 359 from below. The stripper 358 can move in the z direction in the bearing part 368 and is driven, together with the metering shaft 357, by the shaft 359.

The displacement of the metering shaft 357 in the z direction is brought about by two electromagnets 362 and 363, which are mounted on the holding plate 354 and bear a cover plate 366 via two support parts 364, 365. The cover plate 366 is connected to the bearing part 368 fixedly in the z direction, a ball bearing 361 enabling the bearing part 368 to rotate on the rotationally fixed cover plate 366. On activation, the electromagnets 362, 363 generate a force in the z direction and raise or lower the cover plate 366 and as a result the bearing part 368 and the metering shaft 357.

The motor 360 and the electromagnets 362, 363 are controlled by a control part 367, which is arranged laterally on the bearing part 352 and to which the motor 360 is secured.

Moreover, a balance 369 with a minimum weighing range from 0 to 2 kg and an accuracy of 0.1 g, which is in contact with the carriage 353 via a pin 370, is attached to the bearing part 352. Balances of this type are commercially available, for example from Sartorius AG, 37070 Göttingen, Germany. However, it is preferable to use a more accurate balance with an accuracy of 0.1 mg.

If substance which is stored in the metering housing 355 is dispensed via the conical metering opening in the intermediate base 371, the weight load applied to the carriage 353 is reduced and the carriage 353 is pulled downward less strongly, a fact which is measured by the balance 369 via the pin 370.

A second balance 374 is secured to the control part 367 by means of a connecting part 373. The balance 374 bears, via a rotary axle 376 extending in the z direction, a tiltable spoon 375, the concave part of which is located vertically below the metering housing 355.

Substance which has been dispensed by the metering housing 355 firstly drops into the concave part of the spoon 375, so that its weight can be measured there by means of the balance 374. If the measured weight corresponds to a quantity of substance which, by way of example, is to be metered to a reaction vessel, the substance is added to the reaction vessel as a result of the spoon 375 being tilted through 180° as indicated by arrow G. If the weight corresponds to a quantity of substance which is smaller than the quantity desired, either first of all the quantity of substance which is present is added to the reaction vessel as a result of the spoon 375 being tilted, and then the spoon 375 is rotated back into the receiving position and the differential quantity which is still missing is weighed out in a second step, and finally this quantity is added to the reaction vessel, once again as a result of the spoon 375 being tilted, or, as an alternative, more substance is fed direct to the concave part of the spoon 375 until the desired quantity is reached. On the other hand, if the measured weight corresponds to a quantity of substance which is greater than the desired quantity, either the concave part is, as a result of rotation of the rotary axle 376 and therefore of the spoon 375 attached to it in the direction of arrow H, rotated away, emptied, rotated back under the metering housing 355 and refilled with substance, or, as an alternative, the entire solids-metering head 350 is displaced over the tool holder 1, the concave part is emptied, is guided back under the metering housing 355 as a result of displacement of the solids-metering head 350 and is refilled with substance.

The balances 369 and 374 can in each case either be used on their own or together in order to check one another, the balance 374 having the advantage of measuring a smaller total weight. In principle, however, it would also be possible for the rotary axle 376 to be mounted directly on the connecting part 373 and for it, together with the spoon 375, to be controlled purely on the basis of the measurement results from the balance 369.

As an alternative to the spoon 375, by way of example a vessel, e.g. a funnel, which has a closable opening at the bottom, is also conceivable.

A solids-metering head of this type, but without magnet coupling to the tool holder 1, without spoon 375 and without balances 369 and 374 arranged directly on the solids-metering head, is marketed by Auto Dose SA, CH-1228 Plan-les-Ouates.

FIGS. 19 to 23

In this exemplary embodiment, the tool is formed by a screw metering head 420, which can be connected to a tool holder 401, which is secured to the rotary drive 2, by means of a bayonet connection. The bayonet connection comprises, on the tool holder side, an annular connecting part 411 with a connecting bolt 412 and, on the tool side, an annular connecting part 421 with a recess 422 for receiving the connecting bolt 412. Moreover, on the tool side there is a mandrel 424 which is intended to engage in the annular connecting part 411 and stabilizes the bayonet connection.

Via eight contact locations 413, which are distributed over the outer circumference, on the annular connecting part 411 on the tool holder side and eight contact locations 423, which are distributed over the inner circumference, on the annular connecting part 421 on the tool side, the screw metering head 420 can be supplied with power via the annular connecting part 411 and data communication can take place. For its part, the annular connecting part 411 is connected via a cable 414 to the fixed part of the device.

The screw metering head 420 comprises a weighing unit with a housing 425, in which the control electronics 426 and a balance 427 are arranged. It is preferable to use a balance with an accuracy of 0.1 mg. As can be seen from FIG. 20, a bearing part 428 of the balance 427 projects out of the housing 425. A metering unit 430 rests on the bearing part 428 via a drive unit 440 and in this way is weighed, together with the drive unit 440, by the balance 427.

To increase the weighing accuracy, a second balance, which measures the influence of any vibrations, which is then subtracted from the measurement result of the balance 427, can be used in addition to the balance 427.

A filling connection piece 450 is held removably beneath the metering unit 430 by a holder 451 which is fixedly connected to the housing 425. The filling connection piece 450 does not touch the metering unit 430 and therefore does not have any adverse effect on the weighing operation. The fact that it is separate from the metering unit 430 means that the balance 427 is subjected to load from a lower weight, with the result that the weighing accuracy is increased. Moreover, the metering unit 430 and the filling connection piece 450 can be removed and stored separately from the drive unit 440 and the holder 451, respectively.

Alternatively, it would also be possible to use a filling connection piece which is connected to the metering unit 430, which would have the advantage that any residual substance which has remained in the filling connection piece would also be weighed.

Figure 21:
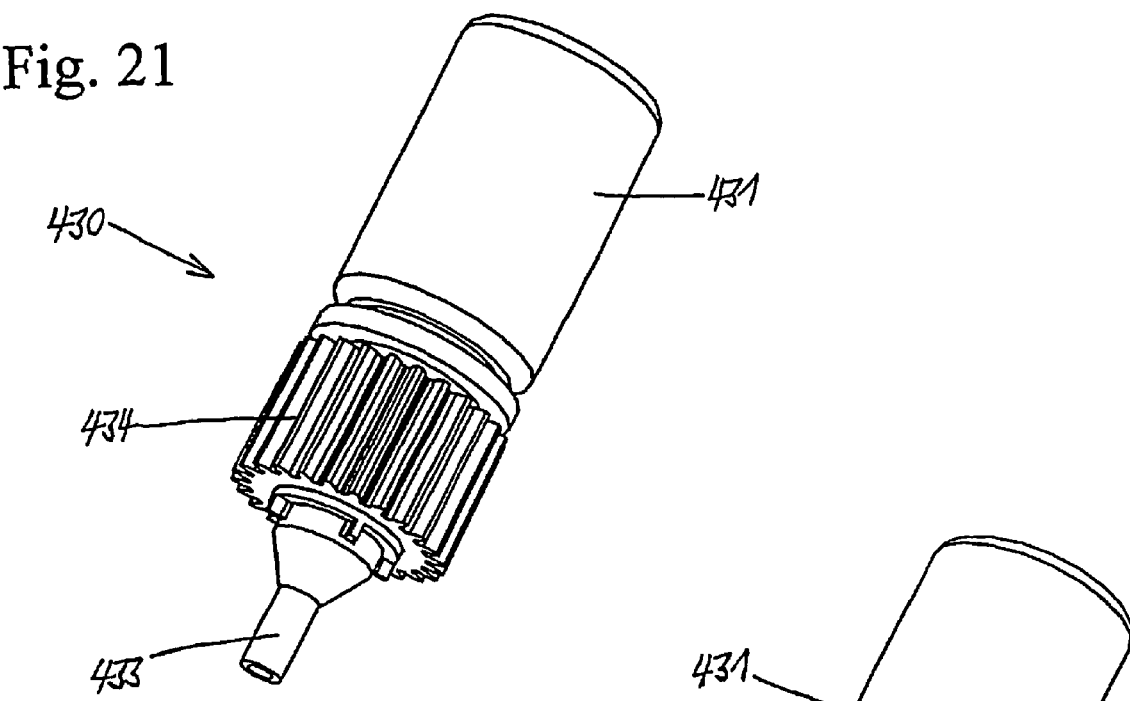
FIG. 21 shows a perspective view of the metering unit of the screw metering head shown in FIG. 19.
Figure 22:
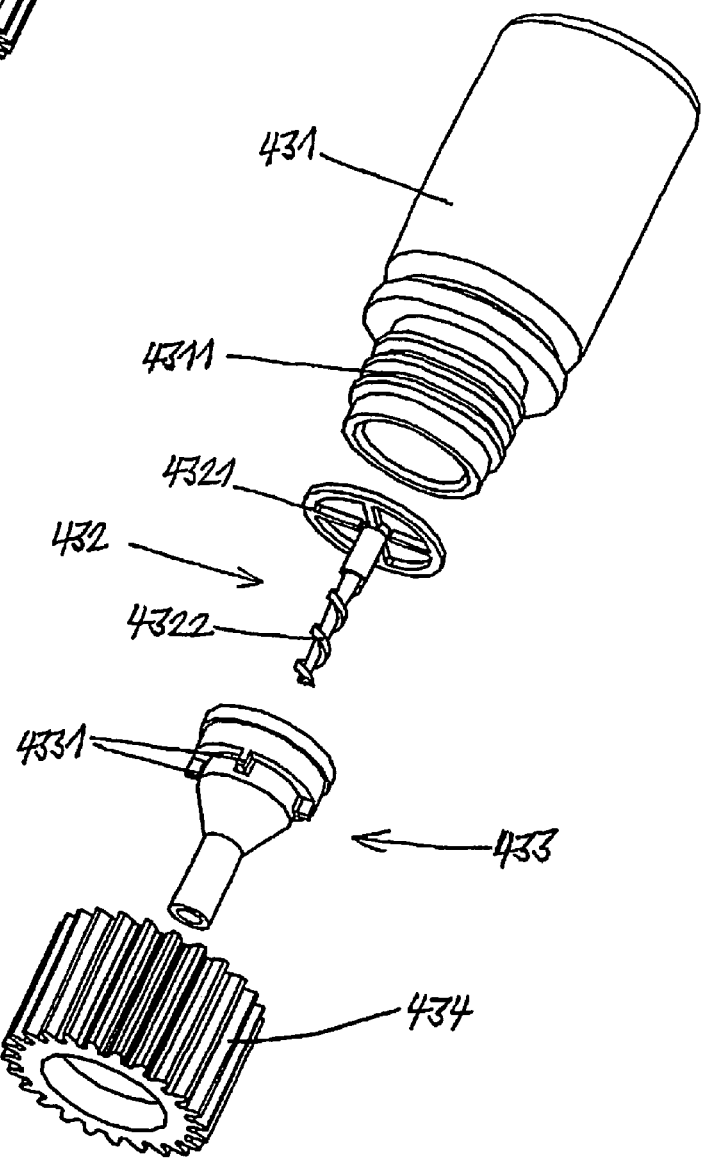
FIG. 22 shows the metering unit of the screw metering head shown in FIG. 19 in an exploded view.

The structure of the metering unit 430 can be seen from FIGS. 21 and 22. The metering unit 430 comprises a storage vessel 431, an extruder 432 having a screw part 4322 and a web part 4321, a metering funnel 433 and a cover 434 which is provided with toothing. The screw part 4322 tapers from the top downward, i.e. away from the web part 4321, with the result that when pulverulent substance is being metered, this substance does not clump together as it passes through the metering funnel 433. The toothed cover 434 has an internal screw thread and is screwed onto a screw thread 4311 of the storage vessel 431, the extruder 432 being clamped between cover 434 and storage vessel 431. The clamping is effected by means of the web part 4321, from which, moreover, strippers, which are not shown in FIG. 2, preferably extend toward the screw part 4322. The metering funnel 433 is held rotatably between cover 434 and extruder 432 and has lugs 4331 which, when the metering unit 430 is inserted in the drive unit 440, engage in recesses 4411 of a metering-unit receiving part 441 of the drive unit 440.

The drive unit 440 also comprises a motor 442 which is secured to a printed-circuit board 443 provided with control electronics and actuates a transmission gearwheel 444. The transmission gearwheel 444 engages through a gap in the metering-unit receiving part 441 in the toothed cover 434 of the metering unit 430 and rotates the toothed cover 434 together with the storage vessel 431 and the extruder 432, while the metering funnel 433 is held in a fixed position by the lugs 4331 engaging in the recesses 4411. The resultant relative movement between metering funnel 433 and extruder 432 causes substance to be conveyed out of the storage vessel 431 through the metering funnel 433 into the filling connection piece 450.

Figure 19:
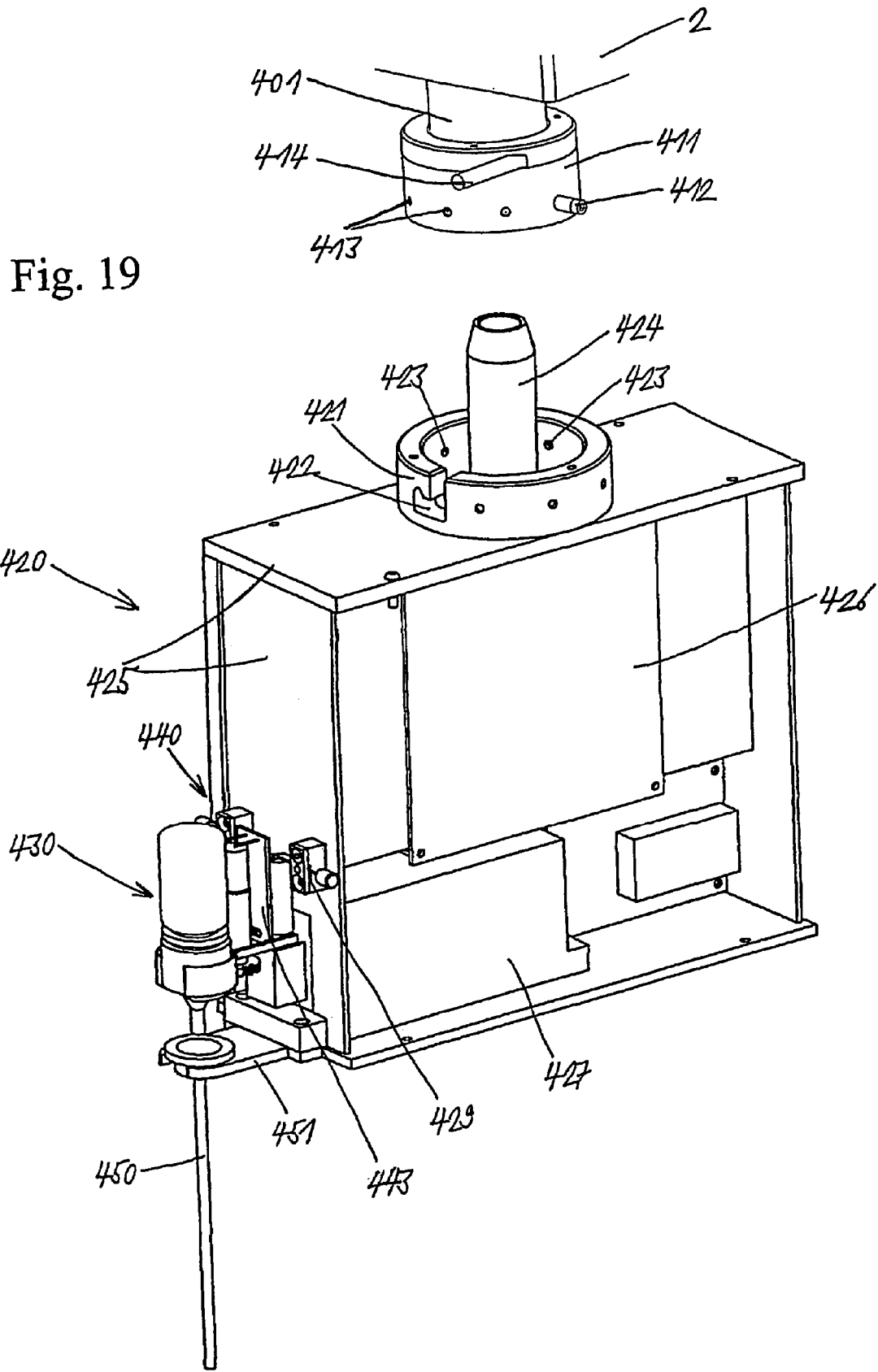
FIG. 19 shows a tool holder with an alternative screw metering head with weighing unit, metering unit and drive unit as tool.
Figure 20:
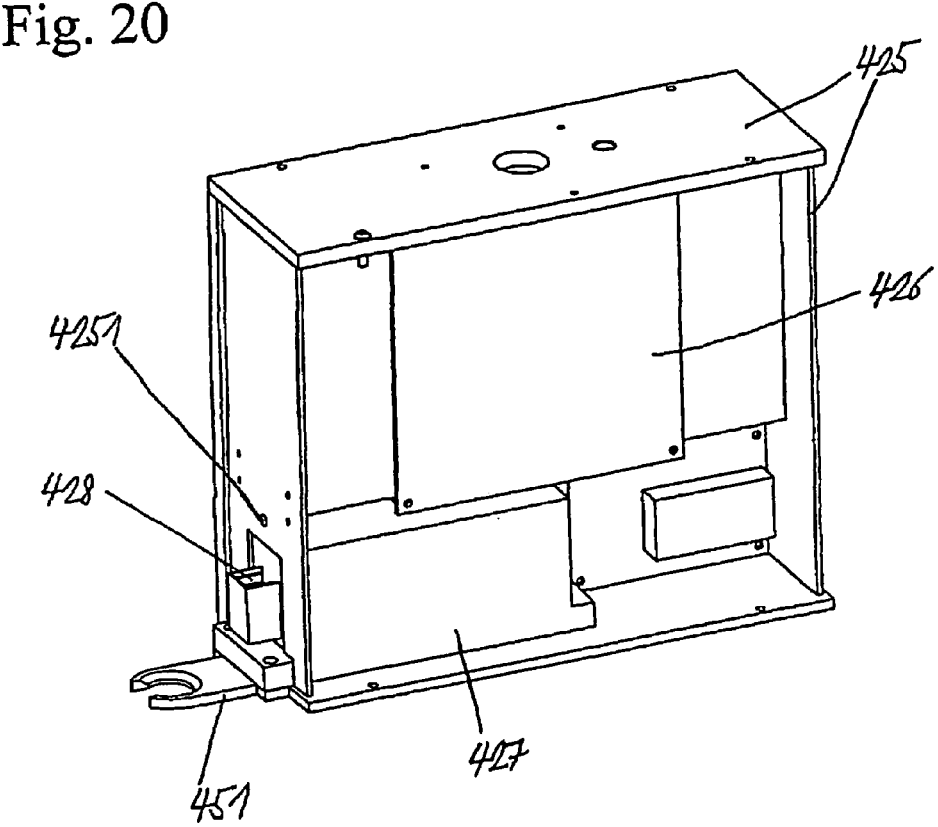
FIG. 20 shows the weighing unit of the screw metering head shown in FIG. 19.
Figure 23:
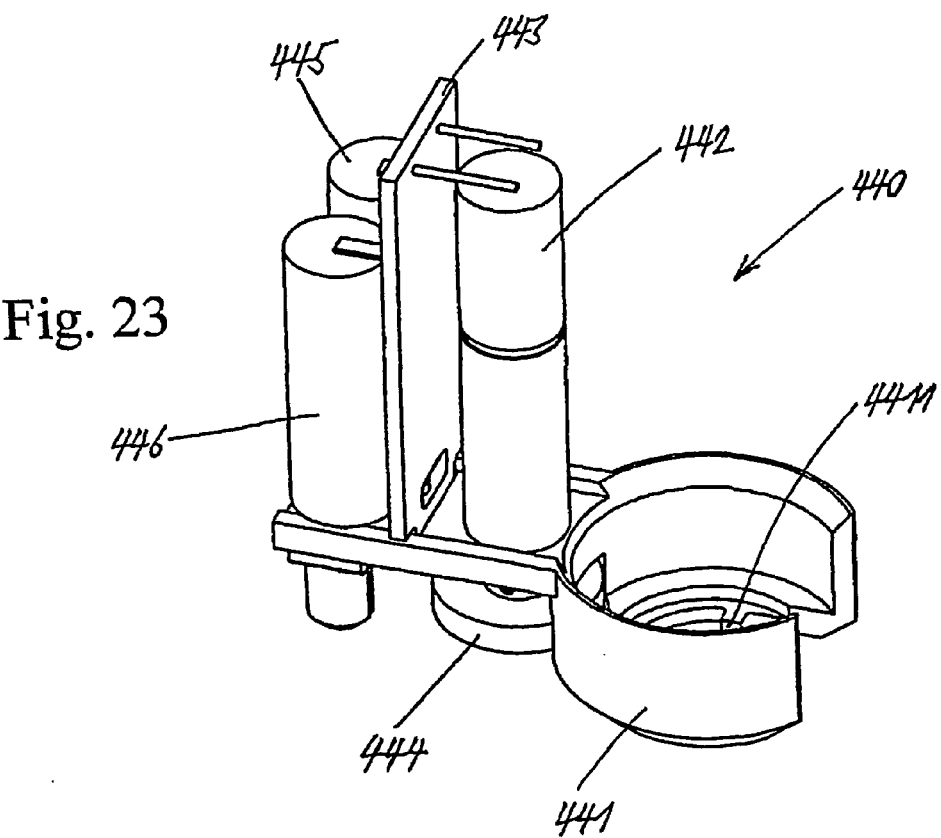
FIG. 23 shows the drive unit of the screw metering head from FIG. 19.

The motor 442 is fed by two storage batteries 445 and 446, which, by way of example, can be recharged by the charging means 429 which is shown in FIG. 19 and is attached to the housing 425. The charging device 429 is designed as a switch and is only in contact with the storage batteries 445, 446 while they are being charged. During the weighing operation, the charging means 429 does not touch the storage batteries 445, 446, so that the weighing operation is not adversely affected.

Alternatively, the charging of the storage batteries 445, 446 could also take place in a separate charging station which is separate from the screw metering head 420, in which case the drive unit 440, to this end, would simply have to be lifted off the bearing part 428 of the balance 427 and transported to the charging station.

The motor 442 is controlled by means of the printed-circuit board 443, which for its part receives control signals from the control electronics 426 arranged in the weighing unit. The transmission of signals from the weighing unit to the printed-circuit board 443 is effected by means of light through an opening 4251, which can be seen in FIG. 20, in the housing 425, so that mechanical contact between weighing unit and drive unit 440 is avoided and the weighing operation is not adversely affected.

The screw metering head 420 can be modified in various ways. In particular, by way of example, the storage vessel 431 can be fixed in such a way that it does not also rotate during the metering operation. In this case, it is also preferable for a driver to extend into the storage vessel 431 from the rotating extruder 432.

The metering may generally take place continuously, but periodic additions of substance and a weighing operation between the individual addition operations are also possible. Moreover, it is conceivable for the storage vessel 431 to be shaken during the metering operation, so that the pulverulent substance contained therein is loosened.

It is possible to execute further design variations on the devices according to the invention which have been described above. Express mention should also be made of the following at this point:

In all the exemplary embodiments described, the balance or balances may be provided either on the tool or on the tool holder 1. Arranging the balance on the tool holder 1 has the advantage that, in the event of a tool change, there is no need for each tool to have a balance. However, this solution means that the weight of the entire tool is always measured as well. By contrast, arranging the balance on the tool has the advantage that in each case a lower overall weight is measured. This tends to make the measurements more accurate.

The connection between tool holder 1 and tool may also be formed in a different way than with magnets or bayonet connections. By way of example, screw connections or clamping connections are conceivable. However, it should be possible for the connection to be produced and released again automatically, i.e. not by hand.

In addition to the tools described, it is also possible to use further tools which are equipped with a connection point to the tool holder and possibly a balance.

The invention claimed is:

1. A device, comprising:
a movement apparatus;
a displaceable tool holder, the tool holder being operatively coupled with respect to the movement apparatus so that the tool holder is displaceable along an x axis or a z axis, the z axis being perpendicular to the x axis;
a tool in the form of a metering head that is secured to the tool holder, the tool being configured to carry a variable amount of a substance; and
a displaceable balance that is configured to weigh variable amounts of the substance while being carried by the tool at a plurality of different locations, the displaceable balance being operatively coupled to the tool holder so that the displaceable balance moves with the tool holder and is available continuously for accurate measurement independently of the position of the tool holder.

2. The device as claimed in claim 1, wherein the substance can be dispensed or taken up by a metering means which is also weighed by the balance.

3. The device as claimed in claim 1, wherein the metering head carries with it all the substance which is to be dispensed.

4. The device as claimed in claim 1, wherein the tool is releasably attached to the tool holder.

5. The device as claimed in claim 2, wherein the metering means is arranged on the balance and is releasably attached to the balance.

6. The device as claimed in claim 2, wherein the metering means has a metering unit and a drive unit, the metering unit further including a storage vessel, wherein the metering unit is releasably attached to the drive unit.

7. The device as claimed in claim 1, wherein the balance bears a vessel for temporarily holding substance which is to be dispensed, which vessel is configured to be completely emptied.

8. The device as claimed in claim 7, further including a second balance, the second balance bearing the vessel for temporarily holding substance which is to be dispensed, and being used to measure the weight of substance to be dispensed which is being temporarily held, while the first balance is adapted to measure the weight of substance which has not yet been dispensed to the vessel for temporarily holding substance which is to be dispensed.

9. The device as claimed in claim 1, wherein the tool holder can rotate about the z axis.

10. The device as claimed in claim 1, wherein the tool is a screw metering head further including a screw disposed within a hollow tube and configured to rotate within the tube, said tube being at least partially open at its lower end and configured to take up and dispense substance as the screw rotates.

11. The device as claimed in claim 10, wherein the lower open end of the tube is closed off by a diaphragm having holes, and a ram operatively coupled to the screw configured to press substance through the diaphragm as the screw rotates when substance is being dispensed.

12. The device as claimed in claim 11, further including a stripper located by the diaphragm configured to periodically strip off substance adhering to the diaphragm.

13. The device as claimed in claim 1, wherein the tool is a capsule-transporting head configured to pick up and release a capsule.

14. The device as claimed in claim 1, wherein the tool is a matrix-capsule-transporting head configured to pick up and release either individually, together or in groups, the capsules arranged in the form of a matrix.

15. The device as claimed in claim 1, wherein the tool is a capsule-handling head configured to pick up at least one capsule, open the capsule in the tool, and mix in the tool the contents of the capsule with another substance.

16. The device as claimed in claim 1, wherein the tool is a matrix-capsule-handling head configured to pick up a plurality of capsules, open the capsules in the tool, and mix in the tool the contents of any capsule with another substance, said capsules arranged in the form of a matrix.

17. The device as claimed in claim 1, wherein the tool is a capsule-dispensing head adapted to store a plurality of capsules, said dispensing head configured to dispense said capsules individually, together or in groups.

18. The device as claimed in claim 1, wherein the tool is a needle head with a hollow needle, a multi-needle head with a plurality of hollow needles or a solids-metering head.

19. The device as claimed in claim 1, wherein the tool is a combination head having at least two tool parts, one of the tool parts being a needle head, multi-needle head, capsule-transporting head, matrix-capsule-transporting head, capsule-handling head, matrix-capsule-handling head, capsule-dispensing head, screw metering head or solids-metering head.

20. The device as claimed claim 1, further including
a camera arranged on the tool holder configured to film an area below the tool holder;
a control computer having an image-processing unit configured to evaluate images filmed by the camera, and change a tool based on the evaluation of the images.

21. The device as claimed in claim 1, further including
an infrared analysis unit arranged on the tool holder having an infrared transmitter configured to radiate infrared waves into an area below the tool holder;
an infrared sensor configured to measure reflected infrared waves; and
a control computer having a measured-value-processing unit to evaluate the reflected infrared waves measured by the infrared sensor, the control computer configured to change a tool and/or change a quantity of substance to be metered, based on the evaluation of the reflected waves.

22. The device as claimed in claim 1, further including tool holder for attaching another tool which can be displaced along an x axis and a z axis, which is perpendicular to the x axis.

23. The device as claimed in claim 1, wherein the tool holder can be displaced along both the x and z axes.

24. The device as claimed in claim 1, wherein the tool holder is configured to be displaced along a y axis, the y axis being perpendicular to the x axis and to the z axis.

25. A method for weighing out a desired variable quantity of a substance, comprising the steps of:
a) providing a movement apparatus; a displaceable tool holder, the tool holder being operatively coupled with respect to the movement apparatus so that the tool holder is displaceable along an x axis or a z axis, the z axis being perpendicular to the x axis; a tool in the form of a metering head that is secured to the tool holder, the tool being configured to carry a variable amount of a substance; and a displaceable balance that is configured to weigh variable amounts of the substance while being carried by the tool at a plurality of different locations, the displaceable balance being operatively coupled to the tool holder so that the displaceable balance moves with the tool holder and is available continuously for accurate measurement independently of the position of the tool holder;
b) using the tool to take up an amount of the substance;
c) weighing the substance taken up;
d) calculating a difference between the weighed value obtained and a desired set value;
e) at least partially discharging the substance taken up or taking up additional substance by the tool if said difference lies outside a range of a desired level of accuracy; and
f) repeating steps c) to e) until the difference is equal to zero within the range of the desired level of accuracy.

26. A method to dispense a desired variable quantity of a substance, comprising the steps of:
a) providing a movement apparatus; a displaceable tool holder, the tool holder being operatively coupled with respect to the movement apparatus so that the tool holder is displaceable along an x axis or a z axis, the z axis being perpendicular to the x axis; a tool in the form of a metering head that is secured to the tool holder, the tool being configured to carry a variable amount of a substance; and a displaceable balance that is configured to weigh variable amounts of the substance while being carried by the tool at a plurality of different locations, the displaceable balance being operatively coupled to the tool holder so that the displaceable balance moves with the tool holder and is available continuously for accurate measurement independently of the position of the tool holder; wherein the balance bears a vessel for temporarily holding the substance which is to be dispensed, which vessel can be completely emptied;
b) placing a quantity of substance into the vessel for temporarily holding the substance to be dispensed;
c) weighing the substance in the vessel;
d) calculating a difference between the weighed value obtained and a desired set value;
e) adding additional substance or at least partially emptying the vessel at a location other than an intended metering location and then adding substance again, if the difference lies outside a range of a desired level of accuracy; and
f) repeating steps c) to e) until the difference is equal to zero within the range of the desired level of accuracy; and
g) dispensing any substance which is present in the vessel until the vessel is completely emptied.

27. A method to select a capsule with a desired quantity of substance, comprising the steps of:
a) providing a movement apparatus; a displaceable tool holder, the tool holder being operatively coupled with respect to the movement apparatus so that the tool holder is displaceable along an x axis or a z axis, the z axis being perpendicular to the x axis; a tool in the form of a metering head that is secured to the tool holder, the tool being configured to carry a variable amount of a substance; and a displaceable balance that is configured to weigh variable amounts of the substance while being carried by the tool at a plurality of different locations, the displaceable balance being operatively coupled to the tool holder so that the displaceable balance moves with the tool holder and is available continuously for accurate measurement independently of the position of the tool holder; wherein the balance is configured to weigh capsules picked up by the tool;
b) using the tool to pick up a capsule containing the substance;

c) weighing the capsule with the substance;
d) calculating a difference between the weighed value obtained and a desired set value;
e) releasing the capsule from the tool and picking up a new capsule containing a substance, if the difference lies outside a range of a desired level of accuracy; and
f) repeating steps c) to e) until the difference is equal to zero within the range of the desired level of accuracy.

28. The device as claimed in claim 1, wherein the displaceable balance is releasably attached to the tool holder.

* * * * *